US008727776B2

(12) United States Patent
Mehl

(10) Patent No.: US 8,727,776 B2
(45) Date of Patent: May 20, 2014

(54) METHOD FOR PRODUCING DENTURE PARTS OR FOR TOOTH RESTORATION USING ELECTRONIC DENTAL REPRESENTATIONS

(75) Inventor: Albert Mehl, Holzkirchen (DE)

(73) Assignee: Sirona Dental Systems GmbH, Bensheim (DE)

( * ) Notice: Subject to any disclaimer, the term of this patent is extended or adjusted under 35 U.S.C. 154(b) by 1892 days.

(21) Appl. No.: 10/534,340

(22) PCT Filed: Nov. 10, 2003

(86) PCT No.: PCT/EP03/12525
§ 371 (c)(1),
(2), (4) Date: May 10, 2005

(87) PCT Pub. No.: WO2004/044787
PCT Pub. Date: May 27, 2004

(65) Prior Publication Data
US 2006/0063135 A1 Mar. 23, 2006

(30) Foreign Application Priority Data
Nov. 11, 2002 (DE) .................................. 102 52 298

(51) Int. Cl.
*A61C 8/00* (2006.01)
(52) U.S. Cl.
USPC ........................................................ 433/223
(58) Field of Classification Search
USPC ................................................. 433/215, 223
See application file for complete search history.

(56) References Cited

U.S. PATENT DOCUMENTS 5,092,022 A 3/1992 Duret
5,217,375 A 6/1993 Oden et al.
(Continued)

FOREIGN PATENT DOCUMENTS

DE 196 42 247 1/1998
DE 198 38 239 3/2000
(Continued)

OTHER PUBLICATIONS

ZWP Spezial; 4 2001 Dezember 1, Jahrgang; CAD/CAM in der Zahnheilkunde Stand und Perspektiven.

(Continued)

*Primary Examiner* — Ralph Lewis
(74) *Attorney, Agent, or Firm* — Fitzpatrick, Cella, Harper & Scinto

(57) ABSTRACT

The invention relates to a method for producing denture parts or for tooth restoration. According to said method, to reconstruct a tooth requiring repair or a defective condition, at least some of the missing exterior surfaces of denture parts or tooth restorations are adapted to the existing residual tooth material and/or the opposing teeth and/or the position of the neighbouring tooth and/or the occlusion position, by means of the optimisation of a generic dental-model data record of the desired tooth type, thus varying the linear factors of at least the most important components, (determined from the electronic data records of a larger number of measured tooth surfaces by primary axis analysis methods), in such a way that the selected optimisation criteria are fulfilled by the minimisation of an error function. After the successful adaptation of said surfaces to the residual occlusion position and the completion of the data record, the reconstructed denture part or the reconstructed tooth restoration is machine-manufactured.

11 Claims, 12 Drawing Sheets

(56) References Cited

U.S. PATENT DOCUMENTS

| | | | |
|---|---|---|---|
| 5,257,203 | A | 10/1993 | Riley et al. |
| 5,533,895 | A * | 7/1996 | Andreiko et al. ............... 433/24 |
| 5,590,055 | A | 12/1996 | Chapman et al. |
| 5,733,126 | A | 3/1998 | Andersson et al. |
| 5,879,158 | A * | 3/1999 | Doyle et al. .................... 433/24 |
| 6,287,121 | B1 | 9/2001 | Guiot et al. |
| 2002/0015934 | A1 | 2/2002 | Rubbert et al. |
| 2003/0012423 | A1 | 1/2003 | Boland et al. |

FOREIGN PATENT DOCUMENTS

| | | |
|---|---|---|
| DE | 199 23 978 | 10/2000 |
| EP | 0 634 150 | 1/1995 |
| EP | 0 643 948 | 3/1995 |
| EP | 0 667 587 | 8/1995 |
| EP | 1304088 | 10/2001 |
| EP | 1 276 072 | 1/2003 |
| EP | 0 913 130 | 3/2003 |
| WO | 99/59106 | 11/1999 |
| WO | 02 39056 | 5/2002 |

OTHER PUBLICATIONS

Shinji Umeyama; Least-Squares Estimation of Transformation Parameters Between Two Point Patterns; IEEE Transactions on Pattern Analysis and Machine Intelligence, vol. 13, No. 4, Apr. 1991.

Christian R. Shelton; B.S., Computer Science; Stanford University, 1996; Three-Dimensional Correspondence; Submitted to the Department of Electrical Engineering and Computer Science in partial fulfillment of the requirements for the degree of Master of Science in Computer Science and Engineering at the Massachusetts Institute of Technology; May 1998.

Blanz et al., "A Morphable Model for the Synthesis of 3D Faces", SIGGRAPH, pp. 187-194 (1999).

Adolph et al., "Modeling of a Fitting Inlay from Various Information", VMV Stuttgart, pp. 309-316 (2001).

Atick et al., "Statistical Approach to Shape from Shading: Reconstruction of Three-Dimensional Face Surfaces from Single Two-Dimensional Images", Neural Computation, 8, pp. 1321-1340 (1996).

Luthardt et al., "Digitalisierung vollstandiger Kiefermodelle und CAD-Modellation von Okklusalflachen," Originalia; Neue Technologie, pp. 574-580, 1999 (with English Abstract).

Mattiola et al., "Computergenerierte Okklusion von CEREC 2 Inlays und Overlays," Schweiz Monatsschr Zahnmed, vol. 105, pp. 1284-1290, Oct. 1995 (with English Abstract).

G. Saliger, "Designing a CEREC Crown" CAD/CIM in Esthetic Dentistry, Chicago, Quintessence Publishing, pp. 427-440, 1996.

Mehl et al., "Erzeugung von CAD-Datensatzen fur Inlays und Kronen mit funktionellen Kauflachen," pp. 520-524, 1997.

Kunzelmann et al., "Automatische Rekonstruktion von Kauflachen computer-generierter Restaurationen," Zahnarztl. Welt/Runschau 102, pp. 695-703, 1993 (with English Abstract).

Blanz et al., "Face Identification across Different Poses and Illuminations with a 3D Morphable Model," Proceedings fo the Fifth IEEE International Conference on Automatic Face and Gesture Recognition, pp. 202-207, May 2002.

Canadian Office Action dated Oct. 20, 2010 issued in the counterpart application No. 2,505,892—3 pages.

* cited by examiner

Example correspondence points

Example contact points to the antagonist

Producing a dental prosthetic item or tooth restoration

Producing a tooth model

METHOD FOR PRODUCING DENTURE PARTS OR FOR TOOTH RESTORATION USING ELECTRONIC DENTAL REPRESENTATIONS

The present invention relates to a method of producing a general, three-dimensional electronic image of a tooth and a method of producing tooth models, dental prosthetic items, or of making restorations of defective teeth or defective dental prosthetic items.

Various options are available for treating dental defects. One option is the direct application of filling material in the mouth, ie the dentist removes the decay and fills the hole with a filling material during the same sitting. This approach is selected mainly for smaller defects. For larger defects, materials such as metal or ceramics, etc, are preferred, which cannot be fabricated directly in the mouth. In addition, in the case of larger defects, configuring the occlusal surface in the mouth is more problematic and difficult to carry out. Therefore, after preparing the tooth, an impression is taken by the dentist. This impression is sent to a dental laboratory and a plaster model is created. By taking account of the opposing teeth and, if appropriate, the jaw movements in the form of articulators, it is then possible to produce the appropriate tooth restoration or dental prosthetic item. The aforementioned can be, for example, inlays, onlays, partial crowns, crowns, bridges, telescope crowns, partial prostheses, etc. Needless to say, making a restoration of this type is very expensive. After the impression has been taken and the plaster model created with alignment with the opposing jaw, waxing or sintering, embedding, casting or pressing, machining, fitting, and polishing are carried out. The large number of steps and the limited technical facilities in the dental laboratory have the result, on the one hand, that processing errors can occur and the quality of the material in the finished product may not be optimal, and, on the other hand, that not all materials can be processed (eg, heavy-duty ceramics). In addition, the high cost of labor also results in great expense.

Recently, CAD/CAM technology has been viewed as an alternative to conventional production methods, in which the dental restorations and dental prosthetic items are produced with the aid of computer methods. In simple terms, the process involved is made up of:
1. Three-dimensional data acquisition of the preparation, or multiple preparations.
2. Generating a CAD data set of the tooth restoration, ie, designing or computing the shell and/or interactive modeling of the shell on the screen.
3. Machining the finished CAD data set in a computer-controlled milling or grinding machine (eg, CNC) or rapid prototyping systems.

The advantage of a method of this type is obvious:
1. Cost savings through automation and therefore time savings.
2. The use of materials that are available in industry. These can be sintered, cast, etc, in more optimal conditions than are present in the laboratory and therefore have better material characteristics. These advantages have already been exhaustively investigated, specifically for ceramics and titanium.
3. A denture is produced having consistent quality. No fluctuations as a result of processing errors arise, as is the case with conventional production processes.
4. Entirely new materials such as zirconium oxide ceramics etc, that hitherto could not be processed at all using the conventional dental process or only at great expense can be fabricated using the CNC method.

Some systems are already in use. A current survey can be found by way of example in a Number of ZWP (December 2001, Mehl). Furthermore, the Patent Specifications U.S. Pat. No. 5,217,375, EP 0643948, EP 0634150, EP 0913130 A2, and WO 0239056 describe systems of this type or individual aspects of systems of this type.

One problem that has not yet been solved is production using the greatest possible degree of automation of dental restorations that already have an occlusal surface, that satisfy all the functional and morphological criteria of an occlusal surface, and that can be optimally adjusted to the state of the opposing teeth.

In most systems, it is currently only possible to manufacture dental frameworks. Similar to the conventional approach, in which, for example, a metal framework is filled out with ceramics or plastics material (this applies also to other materials such as special ceramics or plastics frameworks), the basic framework is generated in the CAD/CAM process and subsequently at least parts of the occlusal surface and other missing exterior surfaces are conventionally filled in using ceramics, composites, etc. These frameworks can be produced, eg, in the CAD software (design software) by enlarging the preparation or computing a surface, which lies at a specific, selectable distance (equal to the layer thickness of the frame) from the preparation surface. In addition, it is also possible to include "convexities" and "deformations". EP 0913130 A2 in FIG. 13b discloses an approach of this type. EP 06 43 948 A1 describes another example.

No method is yet available for the automatic generation of an occlusal surface that is configured in accordance with all the desirable criteria and requirements for a good tooth restoration or dental prosthetic item. However, this is especially desirable because in this way the usefulness and cost efficiency of a CAD/CAM system would be increased and, above all, the CAD/CAM technology could be established on a large scale in dentistry. At the same time, this method would also have to make it possible to produce the computed dental prosthetic items in a machine.

Various methods for shaping an occlusal surface are described in the literature and in patent specifications. For the reconstruction of inlay surfaces, both linear methods as well as various extrapolation methods are described (Mattiola, A., Mörmann, W. H., and Lutz, F, "Computerunterstützte Okklusion von Cerec 2 Inlays und Overlays" (Computer-supported Occlusion of Cerec 2 Inlays and Overlays) Schweiz. Monatssch. Zahnmed. 105: 12831290 (1995); Kunzlemann, K. H., Mehl, A., Pelka, M.: "Automatische Rekonstruktion von Kauflächen computergenerierter Restaurationen" (Automated Reconstruction of Occlusal Surfaces of Computer-Generated Restorations) Zahnärztl. Welt/Rundschau 102, 695703 (1993)). In the linear method, opposite points on the cavity border (usually in the oro-vestibular direction) are joined simply by a straight line and thus the defect is filled in. In extrapolation, the gradient of the still existing remaining tooth structure is continued into the defect, and thus the surface is reconstructed. It is obvious that this approach can only approximately yield a result resembling an occlusal surface. It is not possible to include morphological criteria or the condition of the opposing teeth. At the same time, this method is only suitable for relatively small defects.

A second option lies in further three-dimensional optical scanning either of the existing occlusal surface, before the tooth is ground, or of an occlusal surface that is modeled individually using wax or plastics material (eg, Mattiola, A., Mörmann, W. H., and Lutz, F., "Computerunterstützte Okklusion von Cerec 2 Inlays und Overlays" (Computer-Supported Occlusion of Cerec 2 Inlays and Overlays) Schweiz.

Monatssch. Zahnmed. 105: 12831290 (1995), Mehl, A., Gloger, W., Hickel, R., "Erzeugung von CAD-Datensätzen für Inlays und Kronen mit funktionellen Kauflächen" (Creating CAD Data sets For Inlays and Crowns Having Functional Occlusal Surfaces) Deutsch Zahnärztl. line 52, 520524 (1997)). By clicking on or selecting reference points on the adjacent teeth, the scanned preparation and the scanned occlusal surface can be positioned relatively to each other, and the entire restoration can be built up. In this case, however, a wax model must be produced manually, which means that the automation advantages of using the CAD/CAM system are no longer afforded. In most cases, when treating a tooth, the initial occlusal surface will not be usable due to existing decay defects or insufficient pretreatment, so that this option remains restricted to a limited area of applicability. A further option is presented in WO 0239056. This describes a patient archiving system, eg, a chip card for the patient, which contains stored dental records. These dental data can then be used at a later time when prostheses are manufactured for the patient, and they can serve for reconstructing the defect. In any case, it is assured that the built-up occlusal surface is optimally adjusted to the gnathological system both morphologically and functionally. But, using these methods, corresponding long waiting times must be expected, so that for the treatment of a large population other methods must currently be considered.

Other options involving the inclusion of occlusal surface geometries in the CAD/CAM process are described in the following inventions. DE 198 38 239 A1 describes groups of blanks for dental restorations, which can be assigned to various tooth types and whose external geometries are determined for the specific tooth types from average values that are derived from the relevant textbooks. However, this does not involve a mathematical description of tooth surfaces that can be used for the CAD/CAM reconstruction of tooth restorations, but rather concerns an approximate maximum-minimum estimate for the rough exterior mass of molded blanks, from which the desired individual tooth restoration can be milled. In addition, the average values that can be taken from the literature are only the length, width, or similar linear measurements, which cannot even approximately describe an occlusal surface for the computer-supported reconstruction process.

DE 199 23 978 A1 discloses a method of the computer-supported, patient-specific representation and planning of dental and/or dental prosthetic work, in which a digitized image database is generated using a multiplicity of model tooth and jaw views, the model views including healthy objects and those with disease findings, eg, individual teeth. Such an image database contains images of typical mouth regions. This method functions as a computer-supported expert system for arriving at diagnoses and treatment schedules in dental work. For the three-dimensional reconstruction of tooth defects, such as is necessary in the CAD/CAM process for producing dental prostheses, this method is not appropriate because patient-specific findings do not suffice for precise individual adaptation of the image databases. The image database is only designed to make available typical standard forms for discussing treatment schedules with the patient, and modification by combining these data to form a new representative data set is not attempted.

EP 06 43 948 A1 discloses a method of producing a dental restoration, in which a self-learning data library of basic tooth forms is used. In this context, the method limits itself to producing crown frameworks and provides for only learning such parameters as layer thickness, the localization and thickness of convexities, and the approximate course of the preparation line. This simple "learning" does not lead to mathematical or parametric descriptions of tooth surfaces that are suitable for the reconstruction of individual tooth defects having a complete external geometry such as anatomically and functionally shaped inlays, onlays, crowns, and bridges. In particular, this method does not make it possible to take into account the adjacent remaining dentition condition, such as of adjacent teeth and opposing teeth. Furthermore, in this case the shape provided by nature is not imitated, but rather only the physical design parameters of structures are generated as a function of the experience of the dental technician or expert.

U.S. Pat. No. 5,257,203 discloses a method of producing a dental restoration, in which a database of standardized generic tooth shapes is used, these generic tooth shapes typically being computer-based representations of standardized plaster models of teeth. The generic tooth shapes used in this method are not tooth shapes that are derived mathematically or logarithmically from a database and therefore are not generic tooth models as described in the sense of the present invention, but rather are standardized plaster models that are only scanned three-dimensionally, and this data set is used for reconstruction purposes. The disadvantage is here again that no generally valid design principle underlies the standardization, and shaping depends only on the manual dexterity and the experience of individual experts with a resulting limitation of the multiplicity of shapes that arise in nature.

A further option for producing tooth restorations is described in Saliger, G., Designing a Cerec Crown, in Cerec 10 year Anniversary Symposium, ed. W. H. Mörmann, Quintessence, Chicago, 1996 or in DE 19642247. Here the data set of a model tooth is adjusted and adapted to the prepared tooth. Essentially, this model tooth is scaled, translated, and rotated according to the mesial-distal extension of the defect. A resilient deformation can improve the result. Saliger, 1996 (see above), presents a subsequent interactive possibility of rotating and controlling the occlusal surface relatively to the opposing tooth. In addition, the cusps can be changed in their position. All this takes place interactively. Finally, the tooth restoration is carried out by machining.

The problem in all of the aforementioned procedures resides primarily in the following facts:

- Contact points with the opposing tooth are only subsequently established, in that the adjustment is carried out through interactive distribution or the model tooth is modified until there is contact with the shell. This often results in shapes that are completely atypical of teeth, because the model tooth is from the start not optimally adjusted to the overall situation.
- There is no automated process for selecting the best model tooth (in case more than one is available). Currently, that is only accomplished on the basis of visual rules.
- Working and making changes interactively at the monitor yield effects that are difficult to imagine in three dimensions and therefore those with minimal experience in computer work can master this procedure only after a long period of practice and daily use.
- Neither the morphology of the adjacent teeth, or antagonists, nor even the tooth type situated at an opposite position in the same jaw is taken into account. In many cases, this is important to ensure a harmonious incorporation of the restoration in the jaw system.
- Changes in the model tooth through scaling, cusp positioning, and interactive deformations do not necessarily yield tooth-like surfaces.
- For all interactive or automated adjustments there does not yet exist a method that guarantees that, following the modification, an occlusal surface will result that is very similar to a natural tooth. Since the criteria of a functionally and statically good occlusal surface are not yet known to science and have not even been demonstrated, the requirement for every restoration must be that it approximates to the greatest extent possible natural circumstances and forms, so as not to cause any lasting damage to the teeth, the tissue, or the joint.

The aforementioned problems are overcome by the present invention, which makes possible the manufacture of tooth restorations, dental prosthetic items, or tooth models having occlusal surfaces and/or surfaces that greatly approximate a natural tooth and that are optimally integrated in the jaw from functional and morphological points of view, with it being possible to automate the fabricating process to a greater extent, ie, with substantially fewer interactions and in an error-free, ie, user-friendlier manner.

In the present patent specification, dental prosthetic items are understood to be parts or the entirety of total or partial prostheses (eg, telescope prostheses, bracket prostheses, interim prostheses, etc) or implant structures, and tooth restorations are understood to be bridges, telescope crowns (primary and secondary parts), crowns, inlays, onlays, overlays, and partial crowns. Tooth models are used as prosthetic teeth, as independent models, as components used for practice, training, and demonstration purposes or for depiction in electronic or print media. To be distinguished therefrom is the concept of the generic tooth model or generic tooth model data set, as will be explained below.

On the one hand, the present invention creates a method of producing an electronic data set of an average tooth that can be used for producing a dental prosthetic item, a tooth restoration, or a tooth model, according to an example embodiment. In addition, the present invention also creates a method of producing an electronic data set of a generic tooth model that can be used for building up a prosthetic item, a tooth restoration, or a tooth model, according to an example embodiment. Furthermore, the present invention indicates a method of producing tooth models, dental prosthetic items, or tooth restorations, according to an example embodiment. An example embodiment indicates a use of the method of creating a three-dimensional electronic image of the average tooth, or of the method of producing an electronic data set of the generic tooth model. An example embodiment indicates a use of a numerically controlled machine for producing tooth models, dental prosthetic items, or tooth restorations, which machine is controlled by a data set that is obtained in accordance with the present invention. Refinements of the method according to the present invention are indicated in other example embodiments. Example embodiments indicate a device for visualizing, adjusting, and justifying a generic tooth model data set.

An electronic image of an average tooth as obtained according to the present invention, or the data set of a generic tooth model, is especially well-suited as the starting point for producing a dental prosthetic item, tooth restoration, or tooth model, because the average tooth or, in more general terms, the generic tooth model data set is determined by real teeth, unlike a conventional electronic tooth model, which is based on the ideas of the author of the electronic tooth model, which possibly coincide more or less with nature.

For example, if a restoration for a defective tooth is produced with the assistance of an electronic average tooth, or generic tooth model, as obtained according to the present invention, the natural shape of the tooth that is expressed in the average tooth, or generic tooth model, takes precedence and not a tooth model derived from a person's ideas.

For example, in producing a tooth restoration, the average data set, or the generic tooth model, obtained according to the present invention, can be taken as the starting point, and these data sets can be adjusted to the specific tooth being repaired, taking into consideration the remaining parts of the tooth surface of the defective tooth or the remaining dentition condition, in that these data sets are transformed by interactive interventions or by software-controlled automatic systems so as to carry out the aforementioned adjustment to the remaining tooth surfaces of the tooth being repaired or of the remaining dentition condition adjacent the tooth being repaired.

Particularly good starting conditions are obtained for the generic tooth model data set. On the basis of a correspondence analysis, a principal component analysis and a linear combination are carried out in the manner described in these embodiments, from which a generic tooth model data set is produced. With the assistance of the generic tooth model, it is possible to establish the framework within which it is possible to adjust the model data set to the electronic image of the remaining structure of the tooth to be repaired, without deviating from the supply of natural tooth shapes. The generic tooth model data set can be adjusted to the defective part of the tooth being repaired in an interactive manner or completely automatically using software control and processing. If a numerically controlled machine is controlled in accordance with a data set that is obtained in this manner, the result is a physical tooth part which approximates very well the appearance of the former intact surface of the tooth being repaired, and it is possible to achieve this result in a way that is comparatively simple for the dentist or dental technician.

The methods according to example embodiments are concerned with creating one or at least very few generic tooth model data sets, or average teeth, of a specific tooth type (eg, upper jaw No. 6, or even large, medium, and small upper jaw No. 6, etc). These surfaces provide adequate tooth-like reconstruction for a number of situations. Furthermore, the generic tooth model data set makes it possible that every modification that is carried out on this surface under specific criteria (see below) results with high probability in a natural occlusal surface, and that all possible permitted variants of modifications describe the entirety of virtually all of the tooth morphologies that arise in nature. In this context, the number of adjustment variables is small, and the reconstruction of tooth surfaces can be automated.

In this context, this generic tooth model data set, or the average tooth surface are generated by the greatest possible number of data sets of the same tooth type. In general, the electronic data sets can be scanned both two-dimensionally and three-dimensionally. Two-dimensional scanning is carried out, eg, by metric photography, and three-dimensional scanning, eg, by white light strip projection, etc, stereo photogrammetric methods being also conceivable. However, for the reconstruction of defective teeth and defective dental prosthetic items, data sets are required that are scanned in at least three dimensions. Examples of tooth types are molars, premolars, cuspids, and front teeth. However, the tooth type can also be represented by "upper jaw No. 6", "lower jaw No. 4", or "upper jaw No. 1", etc. Moreover, it is also possible to distinguish according to age and abrasion, sex, ethnic group, size of teeth, morphological peculiarities, etc, for example, the groups "upper jaw No. 7 age 50-60 years", "upper jaw No. 6 with and without tuberculum carabelli", "lower jaw No. 3 in female persons", classifications in large, medium, small No. 6, etc, can be examples of a tooth type. It is also possible, eg, to combine adjacent teeth into one (combined) tooth type in order to integrate or to analyze the interrelationships between adjacent teeth. Using the information of the adjacent tooth, it may be possible, for example, to select the tooth surface for the defective tooth or for the defective dental prosthetic item. The concept of tooth type therefore contains extremely variable classification possibilities in accordance with the task at hand, which should be kept in mind when considering the generality expressed in the patent claims.

For a specific tooth type, the respective data sets must, in a first step, be referenced to each other (brought into the same coordinate system and have approximately the same orientation), and between the surface points of one data set correspondences must be found to those in the other data sets. These correspondences occur, eg, between prominent points and structures of the surface. This assignment can be carried out manually, and it can be carried out by searching for and assigning specific characteristic features, distinctive structures (cusp shape, fissure pattern, marginal ridge, etc). In this regard, it is preferable to select a process that automatically locates these correspondence points and/or structures, since up to now no proven metrically ascertainable states exist that actually comprise the prominent points, structures, or characteristics of a specific tooth type. On the contrary, to date there does not exist in the entire professional dental literature any reference to even an approximately mathematical description of tooth surfaces that would be in any way suitable for the CAD/CAM process.

As a possible implementation option, the following method has proven to be feasible: First, the data sets of the scanned tooth surfaces of a specific tooth type are brought into the same coordinate system in order to obtain the best possible starting point for the automatic determination of correspondence points. This can be carried out using matching routines by minimizing the distance error function, in that rotation and translation parameters are measured. After the coordinate transformation has been completed, the correspondence analysis is carried out. From image processing, it is possible here to successfully apply modified algorithms to the optical flow. Furthermore, through the resilient registration, or matching, of specific features (fissures, cusp tips, cusp overhangs, and marginal ridges) between the individual tooth surfaces, it is possible to create correspondences and to locate imaging prescriptions. Finally, the assignment of many points through correspondences among all data sets is achieved.

More precisely, this is specified below with reference to the method of optical flow. The starting point is m library tooth surfaces of a specific tooth type, taken from a tooth library, in the form $z_j(x, y)$, where $j=1, \ldots m$ as scanning data. Also permissible are parametric representations $z_j(u, v)$, where $u=u(x, y)$ and $v=v(x, y)$, where, for example, these can be polar coordinates, etc. Any complicated three dimensional surfaces having undercutting can be approximated piece by piece using the above functions. In a wider sense, descriptions of teeth involving any number of dimensions are permitted for other methods.

Starting from a reference tooth $z_j(x, y)$, where $R \in \{1, \ldots, m\}$, using a correspondence analysis for each point of the reference tooth, the corresponding point on the occlusal surface $z_j(x, y)$ is searched for. This can take place also by linking correspondences in sequence, in that, beginning from one tooth, the correspondence to a further tooth is established, and from this new tooth a further correspondence to a third tooth, and so on. In addition, before every new correspondence determination, a new average tooth can be computed from the available correspondences and can serve as the starting point for the new correspondence analysis. Overall, this can be achieved using an algorithm that automatically locates these correspondences without requiring prior knowledge, according to an example embodiment. One possibility is the method of optical flow (for any 3-D objects other possibilities are described in Shelton, C.R.: 3-D Correspondence. Master's thesis, Massachusetts Institute of Technology, 1998).

The result obtained is for each tooth $z_j(x, y)$ is a corresponding two-dimensional vector field $\vec{v}_j(x, y)$ where $$\vec{v}_j(x, y) = \begin{pmatrix} \Delta x_j(x, y) \\ \Delta y_j(x, y) \end{pmatrix}$$

so that for each coordinate pair (x, y) of the reference tooth $z_R(x, y)$, the corresponding point of the tooth $z_j(x', y')$ is generated from the relation:

$$z_j(x+\Delta x_j(x, y), y+\Delta y_j(x, y)).$$

With respect to tooth surfaces, it is expedient, in addition to the smoothness of the displacement field relative to the z-coordinates, to also require smoothness with respect to the gradients, because gradients also represent an essential feature of the occlusal surfaces. Furthermore, using the correspondence analysis approach, one can also attempt, after finding each new correspondence, to merge this data set with the existing corresponding data sets and to search therein for a new linear combination which approximates to the greatest extent possible the next data set, which is not yet in correspondence. This new linear combination can then be used in the automatic correspondence search process. Thus, in an iterative manner, all data sets can be brought into correspondence.

Since not all the points of a surface can be clearly assigned to the points of another surface, it is possible to require that the displacement field behave graphically like a resilient diaphragm, this being virtually non-displaceable between the unambiguous correspondences, whereas in between, ie, in the areas of unclear or weak correspondences, it can relax quite freely. This can be computed, for example, by minimizing an energy function that arises from coupling of many springs between the individual surface points (approximation for the continuous resilient diaphragm).

One interesting expansion for the computation of the optical flow lies in the fact that, in addition to the three-dimensional data representation z(x, y), other criteria or surface descriptions are consulted for the correspondence analysis, as is indicated in an example embodiment. For example, this could be the gradient field of the tooth surface. Better than height data, gradients describe specific features such as edges, corners, or more pronounced changes in the surface. By creating a new feature vector $\vec{m}$ where $$\vec{m} = \begin{pmatrix} z(x, y) \\ \nabla x(x, y) \end{pmatrix}$$

and introducing a new standard for this feature space:

$$\|\vec{m}\|^2 = z^2(x, y) + \beta(\nabla z(x, y))^2$$

in which $\beta$ establishes the weighting of the gradient field in relation to the relief image, the displacement field $\vec{v}(x, y) = (\Delta x(x, y), \Delta y(x, y))^T$ for the feature vector $\vec{m}$ can be computed by analogy to the above, if the standards $\|\vec{m}_x\|$ and $\|\vec{m}_y\|^2$, and the respective scalar products $<\vec{m}_x, \vec{m}_y>$ and $<\vec{m}_x, \Delta \vec{m}>$ are used. Of course, it is also possible to conceive multidimensional feature vectors, by taking into account further characteristics of the tooth surface. These could be, for example, texture values, curvatures, etc. The weighting factor $\beta$ (or other weighting factors) make it possible to establish the specific influence of the individual feature fields. All of these measures yield a powerful tool, which, for the tooth surfaces, makes possible an automatic analysis of correspondences that does not require prior knowledge.

When these correspondences have been located, the reference tooth, in a next step, can be represented as a vector in 3n-dimensional space (in this context, n equals the number of selected points that lie on the tooth surface), ideally an equidistant grid will be used, and the typical number of points can go from 10,000-200,000):

$$\vec{D}_R = (x_1, y_1, z_R(x_1, y_1), x_2, y_2, z_R(x_2, y_2), \ldots, x_n, y_n, z_R(x_n, y_n))$$

In a consistent manner then, proceeding from the reference tooth (or from the linear combination) and from the corresponding vector field $\vec{v}_j(x, y)$, all other teeth of the library are represented as 3n-dimensional vectors:

$$\vec{D}_j = (x_1 + \Delta x_j(x_1, y_1), y_1 + \Delta y_j(x_1, y_1), z_j(x_1 + \Delta x_j + (x_1, y_1,), y_1 + \Delta y_j(x_1, y_1)),$$

$$x_2 + \Delta x_j(x_2, y_2), y_2 + \Delta y_j(x_2, y_2), z_j(x_2 + \Delta x_j + (x_2, y_2,), y_2 + \Delta y_j(x_1, y_2)),$$

$$x_n + \Delta x_j(x_n, y_n), y_n + \Delta y_j(x_n, y_n), z_j(x_n + \Delta x_j + (x_n, y_n), y_n + \Delta y_j(x_n, y_n)))$$

In this way, the same vector coordinates, ie, indices, also represent the corresponding points, specifically between all teeth. All of the m vectors, which correspond to the m library teeth, span a space that is designated as the tooth space for the corresponding tooth type. Therefore, it is now possible to compute the average tooth $\vec{D}$ from the individual transformed library teeth $\vec{D}_j$:

$$\vec{D} = \frac{1}{m} \cdot \sum_{j=1}^{m} \vec{D}_j$$

At this point, it is possible to use the new average tooth as a reference tooth, start the above process once again, and repeat it many times. In this way, the average tooth can be determined even more generally. Or various reference teeth are taken and the result is subsequently averaged. In an example embodiment, this average data set is made available as an average tooth of a specific tooth group (tooth type) (FIG. 9).

If the individual tooth surfaces are present as vectors, it is possible, with a high degree of probability, to represent each additional tooth $\vec{Z}$ as a linear combination of the existing teeth:

$$\vec{Z} \approx \sum_{j=1}^{m} \beta_j \cdot \vec{D}_j$$

A principal component analysis is available for reducing the number of linear factors $\beta_j$ and of teeth $\vec{D}_j$. Since each tooth type is recognizable to the person skilled in the art through specific features, those components should have great influence as a result of the principal component transformation in characterizing the specific features of the tooth type. Thus, a sufficient description of most tooth surfaces is obtained using the linear combination of part of the principal component. This principal component analysis can be directly carried out on the tooth data $\vec{D}_j$, as indicated in an example embodiment. The implemented portion p of the resulting principal components (usually those that contribute most to the variance) are linked mathematically by a linear combination (linear factors $a_i$ and principal components $\vec{P}_i$) as follows:

$$\vec{Z} \approx \sum_{i=1}^{p} a_i \cdot \vec{P}_i. \quad \text{(Equation 1)}$$

As indicated in an example embodiment, before the principal component analysis is carried out with respect to the tooth vectors, it is possible to displace the vector space such that the average value 0 is generated. This is obtained by carrying out a subtraction operation between the individual tooth vectors and the average tooth. The differential vectors that are generated can then be analyzed also using principal component methods. Overall, using these methods involving only a few variable parameters, an adequately efficient description of new tooth forms is achieved, which can be represented as linear combinations of these new parameters (linear factors) and principal components. The decisive advantage is that, as the parameters change, one of the existing natural tooth data will be approximated with a high degree of probability. Therefore, the restoration to be created will be very tooth-like, and the risk of obtaining bad occlusal surfaces is eliminated.

In what follows, the principal component analysis is described in greater detail with respect to the tooth vectors for the case in which the average tooth is subtracted, ie, the vector space of the teeth is displaced such that the average value 0 is generated. Therefore, even after the principal component analysis, the average values of the principal components (eigenvectors) are 0. From each tooth vector $\vec{D}_j$, the average tooth $\vec{D}$ is subtracted, and a new differential vector $\vec{\Delta}_j$ is generated, where $$\vec{\Delta}_j = \vec{D}_j - \vec{D}.$$

The principal component analysis then supplies the eigenvalues $\lambda_k$ with their associated principal axes (principal components, eigenvectors) $\vec{P}_k$ where k=1, ... m. The following characteristics are produced:

1. Eigenvalues $\lambda_k$ correspond to the variances in the direction of the principal component $\vec{P}_k$.
2. The sum of eigenvalues $\lambda_k$ corresponds to the sum of the variances of $\vec{\Delta}_j$, ie, the total variance of $\vec{\Delta}_j$. Since an average displacement has no influence on the variance of the values, the sum of eigenvalues $\lambda_k$ therefore corresponds to total variance of $\vec{D}_j$.
3. The proportion of a principal component $\vec{P}_k$ of the total variance of the data sets is given by:

$$\lambda_k \bigg/ \sum_{l=1}^{m} \lambda_l$$

4. The proportion of the first p principal components $\vec{P}_k$ of the total variance is by analogy given by:

$$\sum_{l=1}^{p} \lambda_l \bigg/ \sum_{l=1}^{m} \lambda_l$$

For example, in the case of upper molars it is found that the first 7 principal components describe approximately 70% of the total variance of 170 teeth.

A large proportion of all possible tooth surfaces $\vec{Z}$ can now be relatively precisely approximated using a linear combination of the first p principal components $\vec{P}_k$ ($\alpha_l$ being the linear factors):

$$\vec{Z} \approx \vec{D} + \sum_{l=1}^{p} \alpha_l \cdot \vec{P}_l \qquad \text{(Equation 2)}$$

If reasonable limiting conditions are placed on parameters $\alpha_i$, (Equation 1) and $\alpha_l$ (Equation 2) (eg, that the new tooth be located within the space encompassed by the existing teeth or be situated at least not very far from it), any linear combination will describe a tooth in accordance with (Equation 1) or (Equation 2). A tooth data set, which is usually generated by a linear combination of principal components and, if appropriate, by the addition of an average tooth, is designated in this patent specification as a generic tooth model data set, or a generic tooth model, with respect to the tooth type of interest. Synonymous therewith, and in an abstract sense, the generic tooth model data set, or the generic tooth model, is conceived in this patent specification with respect to the tooth type of interest as a combination of data sets of the selected principal components and, if appropriate, of the average tooth. This combination can be conceived either physically, eg, as individual data sets that are joined by links or by references, or by merging the same to form one large data set. If a representation of this generic tooth model, or generic tooth model data set, is desired, it is only necessary to multiply the special linear factors with the principal components and, if appropriate, to add the average tooth. The generic tooth model, or the generic tooth model data set (hereinafter abbreviated as "generic tooth" in some instances), therefore represents a kind of mathematical description of the overall tooth space of the corresponding tooth type.

According to example embodiments, the reconstruction process for the defective tooth or the defective dental prosthetic item can be carried out using the average tooth, or the generic tooth model, and can also be substantially automated. Reconstruction signifies the build up or at least partial repair of the missing shell of the defective tooth or of the defective dental prosthetic item. The defective tooth can be an inlay, onlay, overlay, partial crown, crown, bridge preparations, etc, and the defective dental prosthetic item can concern filling out regions of missing teeth, eg, intermediate bridge members, implant structures, or parts of partial prostheses or total prostheses. The concept of remaining dentition condition in this patent specification designates the scanned information (in particular, data sets) of the prepared tooth or teeth (the tooth or defective teeth) or of the defective dental prosthetic item, and the additional optional inclusion of scanned information of the remaining tooth structure, the opposing jaw, the functional and static/occlusal bite registration, the adjacent tooth/teeth and/or the gum component, or the alveolar ridge. The concept of opposing jaw signifies generally only the inclusion of one or more opposing teeth, ie, the tooth or teeth that are opposite the defective tooth or the defective dental prosthetic item. The concept of opposing tooth is synonymous with the technical term antagonist. However, in this patent specification, the term opposing tooth also includes part of the opposing jaw or the entire opposing jaw. If, from the relevant preparation or defective dental prosthetic item and from the surrounding remaining dentition condition, specific construction points, or correspondence points, or correspondence structures are selected, eg, cusp tips or marginal ridge points on the remaining tooth structure and/or possible contact points with the opposing tooth or adjacent tooth (FIGS. 9 to 11), then, assuming knowledge of the relevant correspondence points and structures on the generic tooth model, average tooth, etc, the reconstruction can best be carried out using optimization processes. On the average tooth, rotation, translation, scaling, and, optionally affine transformation parameters are usually generated using minimization processes. In the case of the generic tooth, there is additional optimized adjustment of the parameters (linear factors) of the principal components such that insertion of the generic tooth, after it has been modified in accordance with the parameters, takes place in an optimal manner. Optionally, it is also possible to build into this process secondary conditions such as limiting the magnitude of the parameters, so that the result does not lie far beyond the tooth space, or the condition that the opposing occlusal surface or functional bite registration should not be penetrated, although it may rest upon the contact points. It is also possible to take into account quality parameters such as minimal layer thicknesses for a material or a surface design having optimal load bearing properties.

In addition to the individual correspondence points, however, it is also possible to locate in their totality all existing remaining tooth surfaces (eg, in the case of inlays, onlays, partial crowns), or alternatively corresponding structures, ie, specific characteristic areas and shapes, and to take all the points of these remaining tooth surfaces and/or structures into the correspondence. This can be carried out, eg, by analogy to the above, using the method of optical flow. Another possibility is to use matching by optimizing the parameters corresponding to a quality function (eg, distance function). In this context, it is again decisive that the tooth be not deformed in any manner but rather remain along the principal components and therefore within the range of the shape of natural teeth.

In general, the generic occlusal surfaces and data sets of the defective dental prosthetic item or of the defective tooth do not lie in the same coordinate system. Therefore, in the generic occlusal surface, in addition to the parameters along the principal components (linear factors), at least rotation and translation must also be determined. It is also possible to include scaling, but this is not entirely advisable in this case because this factor should already have been integrated in the principal component representation. One possibility of solving the problem lies in carrying out the adjustment process in two steps:

1. Rotation and translation of the average tooth into the coordinate system of the defective tooth on the basis of correspondence points and/or remaining tooth structure. This can be carried out, eg, using the algorithm according to Umeyama (Umeyama, S.: Least-squares estimation of transformation parameters between two point patterns, IEEE PAMI 13(4); 276280, 1991), the scaling factor being set at 1.
2. Improving the adjustment of the correspondence points by optimizing the principal component parameters (if appropriate, supplemented by the linear factors of rotation and translation, etc).

The advantage is that direct solutions can be employed for both steps. In the general case (also a one-step solution), it is of course also possible to use familiar nonlinear iterative solutions (eg, gradient decline methods, Levenberg Marquardt, etc).

If the original data set of the remaining tooth structure and/or correspondence points has been translated and rotated into the coordinate system of the average tooth, then, on the basis of the characteristics of the generic tooth surface, optimal initial conditions exist for the reconstruction of tooth surfaces. The objective lies in determining the parameters (linear factors) such that the linear combination (ie, a new occlusal surface) that results is adapted to the existing situation to the greatest extent possible. This is accomplished, eg, by minimizing an error function.

The adjustment can be further optimized by permitting only those linear combinations which show a high degree of probability, ie, that give precedence to the most typical tooth shapes for the tooth space. In this way, the result should lie, with great probability, within the convex shell of the tooth data. Alternatively, it is conceivable in this connection to include probability theory observations. The following conditions should be taken into account:

a) The desired occlusal surface within the space of the tooth surfaces should have the greatest possible probability, ie, its shape should be the most typical possible for an occlusal surface.
b) The measured points may have measuring errors (eg, as a result of measurement or by mouse clicking). In order that a measuring or processing error will not be excessively weighted in the selection of the occlusal surface, here too a probability will be taken into account for a measuring point as a function of noise or error sources.

An approach of this kind could lead to the following maximization of probability:

$$P(\vec{c}|\vec{z}_{real}) = const \cdot P(\vec{z}_{real}|\vec{c}) \cdot P(\vec{c})$$
$$= const \cdot e^{-\frac{1}{2\sigma^2}\|M\vec{c}-\vec{z}_{real}\|^2} \cdot e^{-\frac{1}{2}\|\vec{c}\|^2}$$

This probability is maximized if the quality function E is minimal:

$$E = \|M\vec{c} - \vec{z}_{real}\|^2 + \gamma \cdot \|\vec{c}\|^2 = \min$$
$$\gamma = \frac{1}{\sigma^2}$$

where $$z = \sum_{l=1}^{p} \lambda_l c_l \vec{p}_l = M\vec{c},$$

where the matrix $M = (\lambda_1 \vec{p}_1, \lambda_2 \vec{p}_2, \ldots, \lambda_p \vec{p}_p)$, and the measuring error has a variance of $\sigma^2$. The measured optimal generic tooth surface is very easy to integrate into the given remaining dentition condition. The remaining dentition condition is the scanned information (in particular, data sets) of the prepared tooth, including remaining tooth structure, opposing jaw, functional and static bite registration, adjacent teeth and/or gum line and alveolar ridge. Undoubtedly, even smaller differences will generally be found, such as small steps or gaps in the transition to the remaining tooth structure, excessively elevated points that penetrate the bite registration or the adjacent tooth, contact points that are still missing, etc. In addition, under certain circumstances, surfaces that are still missing such as approximal surfaces, oral and vestibular surfaces can be built up. These processes that are in toto designated as adjustments, which generally involve only slight changes, then supply the finished data set that is used for controlling a machine.

In an example embodiment, the use of these computed data sets is described for the physical production process. In principle, all possible automated production methods can be used such as CNC milling or grinding, laser processing, stereo lithography, or lithographic sintering methods. The material spectrum for the tooth restoration, dental prosthetic items, or tooth models can range from plastics materials to metals (titanium, gold, steel, etc) to ceramics. In dentistry, a series of materials are currently specially available for the CAD/CAM process.

An example embodiment defines the entire production process from scanning to fabrication. Implementation variants as indicated above can be used here by analogy. From the description and the drawings, a person skilled in the art can derive further variants that are not indicated here in detail, so that they can also be regarded as being fully incorporated in this patent specification.

An example embodiment explicitly relates to taking into account functional and/or static or bite registrations. One great advantage of the entire occlusal surface adaptation using mathematical and electronic methods lies in the fact that it is no longer necessary to go through the entire production chain from taking an impression of the opposing jaw, making a plaster model of this opposing jaw, articulating the opposing jaw and assigning to the sawed model or preparation model, down to determining and justifying the jaw joint parameters, etc. The alternative here represents direct modeling of the opposing jaw position by taking bite registrations in the mouth. The static bite registration, sometimes also known as an occlusal bite registration, is obtained by placing molding material at the desired location, the patient then biting down and leaving the teeth in the bite-down position until the material sets. Information regarding jaw movements is obtained by the patient also carrying out the greatest possible number of different jaw movements before the impression material has set. This then generates the functional bite registration, sometimes also termed the FGP (functional generated path). Using this approach, very precise, three-dimensional information is obtained regarding the pathways of the teeth opposite the preparation, and therefore also borderlines and design indications as to where contact points may lie, and where the reconstructed tooth surface should not be expanded, ie, where the highest points might be. According to an example embodiment, it is precisely this information that is consulted for determining correspondence and therefore for more precise adaptation of the average tooth, or the generic tooth. Using appropriate mathematical formulations, this information can be included in the optimization or minimization methods in the form of limiting conditions. This condition could be as follows: Contact points are points (interpolation of the point having a secondary derivation equal to 0) that contact the bite registration, whereas the remaining areas of the reconstructed surface may not be contacted.

An example embodiment describes the possibility of automating the process of locating the contact point with the opposite tooth (antagonist). By comparing the static (occlusal) bite registration with the functional bite registration, both of which were taken from the patient for the corresponding situation as indicated above and are located (referenced) as measured data sets in the same coordinate system, the areas in which the one bite registration is at a short distance from the other bite registration, or where they contact each other, are especially well displayed. These areas represent the possible candidates for contact with the antagonists, and no contact lines will be found in the other areas. If it is known where the corresponding contact points are located on the generic tooth surface, or on the average tooth, then it is possible to automate the optimization of the linear factors to a substantial extent.

According to an example embodiment, for the approximal surface configuration (eg, position of the approximal contact, extension, etc) and for the selection of the correspondence points or structures (eg, marginal ridges, shapes of the occlusal surface, etc) the scanned information of the adjacent teeth is also included. Similarly, individual points (eg, contact points) or the shape and structures of the opposing tooth can be used for the creation of correspondence, and thus the selection of the best fitting tooth surface can be carried out for the reconstruction of the defective tooth or the defective dental prosthetic item. Similarly, information on the corresponding, symmetrically opposite tooth could be taken into account, because it is often presupposed that these tooth shapes are only mirror images showing great resemblance to each other. In particular, this example embodiment includes the possibility of drawing conclusions concerning the shell to be built up or at least parts of this shell, from the information concerning the adjacent tooth/teeth on the basis of the interrelations that are found, from the principal component analysis or correspondence analysis, to exist between adjacent teeth of the same patient (eg, for creating the generic tooth model of adjacent teeth). One possibility lies in optimizing the parameters of the combined generic tooth model data set when adapting to the adjacent tooth/teeth, while at the same time modifying the tooth surface to be reconstructed, to an appropriate extent. The same method can be used for the opposing tooth, or the symmetrically opposite tooth. In particular, this example embodiment makes reference to the fact that the information regarding adjacent tooth/teeth, opposing tooth and/or symmetrically opposite tooth/teeth can also consist of two-dimensionally scanned data sets. Based on these data sets, it is possible to form conclusions concerning the three-dimensional structure with the assistance of a corresponding generic tooth model through the optimization of imaging, illuminating, rendering, and/or projecting functions (eg, see Blanz, V., Romdhani, S.: Face Identification across Different Poses and Illuminations with a 3-D Morphable Model. Proc. Int. Conference on Automatic Face and Gesture Recognition, 202-207, 2002) and to use them for the reconstruction. The advantage of this two-dimensional scanning lies in the fact that images or data sets can be created relatively easily, eg, using an intraoral camera or photographic equipment on the patient.

An example embodiment indicates that necessary adjustments can still be carried out if undesirable areas and irregularities are still present after computing the best-fitting generic tooth, or average tooth. Such features may comprise small steps or gaps in the transition region leading to the remaining tooth structure, points that are too elevated and penetrate the bite registration or the adjacent tooth, contact points that are still missing, etc. For this purpose, methods are available that ensure that the modifications remain locally delimited and as small as possible, whilst at the same time producing a harmonious and smooth transition to the unmodified regions. This can be carried out using familiar deformation and/or morphing methods. In addition, under certain circumstances, the missing surface parts such as approximal surfaces, oral and vestibular surfaces can be built up. Possible methods of automatically building up these surfaces are described below. All of these processes can be carried out automatically or interactively. In interactive manipulation, the dentist or dental technician can still optimize the configuration in accordance with his or her ideas. Usually, this possibility should always be implemented in methods for producing dental prosthetic items or tooth restorations.

With the assistance of the generic tooth, various occlusal and functional concepts can be realized. In dentistry there are various theories about where the static and functional contact lines to the adjacent tooth or antagonist are to be found. The generic tooth provides the opportunity to decide, quasi online, which concept is to be preferred and where the contact lines should be (FIGS. 9-11). In this context, for example, the desired contact lines are marked on the generic tooth, the corresponding correspondence points on the bite registration and/or the remaining tooth structure or adjacent tooth, as indicated in an example embodiment either once and for all for a specific user or laboratory favoring a specific concept, or alternatively before each new treatment. By adjusting the parameters with regard to the corresponding points, a functionally configured natural occlusal surface is obtained after the minimization methods have been employed. This method functions only when using generic teeth, because in the case of tooth libraries, the best tooth can only be selected if, due to changes in the contact/functional situation, the corresponding reference points of all teeth have to be determined anew, which is an expensive undertaking, given the large number of teeth. On the other hand, in the case of deformation of only one model tooth not created on the basis of a generic tooth and in cases where if the principal component analysis has not been carried out, there can be no assurance that the work will produce a harmonious, tooth-like result.

Example embodiments describe a method of producing dental prosthetic items, which, proceeding on the basis of 3-D data sets of the opposing jaw situation (FIG. 2) and the preparation (FIG. 1) or multiple preparations, which are referenced to each other, are created in that the most fitting occlusal surface is automatically selected from a tooth library (FIG. 5) after referencing the existing bite registration to the preparation data sets on the basis of the possible overlapping areas (FIG. 3), following the selection of the most appropriate correspondence points (FIG. 4). An error minimization method of the selection and adaptation of a library occlusal surface that is very well-suited for this purpose and does not proceed in an interactive manner is described, eg, in Umeyama (Umeyama, S.: Least Squares Estimation of Transformation Parameters between Two Point Patterns. IEEE PAMI 13(4): 276280, 1991). Subsequently, existing interferences or overcuttings relative to the opposing tooth row and/or adjacent teeth are eliminated, and in the case of inlays, onlays, and any partial crowns, the remaining tooth structure is also taken into account, the missing exterior surfaces are built up (FIGS. 6 and 8), and they are then adjusted to the preparation line such that a virtually smooth, harmonious transition is achieved (FIG. 7). By fusing the exterior and interior surfaces along the preparation line (marginal curve), the dental prosthetic items can then be machined. The first decisive factor is that in comparison with the above-mentioned, familiar methods, as a result of selecting many different teeth from a tooth library, it is not the tooth that is adjusted to this situation but rather a tooth is selected that is already very well adapted to this situation, in which it is then only necessary to carry out very small adjustments, which are therefore less error prone and easier to automate. The second advantage is the separation of important or complicated parts of the tooth surface from less important or simpler parts. The former involves, eg, the occlusal surface, and the latter concerns the vestibular, approximal, and oral surfaces of the teeth. As a result of this division, it is possible to restrict oneself to better adaptation of the more complicated surfaces obtained from the tooth library, while the exterior surfaces are automatically built up and reconstructed. For the exterior surfaces, it is sufficient to indicate only a few construction points (FIGS. 8 and 16). One implementation possibility is the computation of Bezier, NURBS, or B-spline surfaces, which adjoin continuously and smoothly the corresponding parts of the preparation limit and the border of the integrated library data set and that interpolate the construction points (such as approximal contact or convexities of the vestibular or oral surfaces). An example embodiment specifies this method.

An example embodiment specifies how this tooth library can be set up. In this context, it is expedient to have a structure in which a data set, which contains the type and the features that are to be taken into account for the selection, is assigned to each tooth data set either through referencing or through being given an appropriate name. In addition, a library is designed to be made up of tooth surfaces that derive from natural, cavity-free, and intact teeth.

The most general form of a tooth library contains the entirety of all possible tooth shapes that arise either naturally or artificially. The tooth library is sensibly divided into groups of different tooth types. This subdivision in accordance with tooth type can involve, for example, molars, premolars, cuspids, and front teeth. Alternatively, the type can be designated as upper jaw No. 6, lower jaw No. 4, upper jaw No. 1, etc. Furthermore, it is also possible to distinguish according to age and abrasion, gender, ethnic group, size of teeth, morphological peculiarities, etc; for example, "upper jaw No. 7 age 50-60 years", "upper jaw No. 6 with and without Tuberculum Carabelli", and "lower jaw No. 3 in females", can represent examples of tooth types. The concept tooth type therefore includes extremely variable possibilities for classification depending on the task at hand.

An example embodiment describes a method in which, in creating the generic tooth model data set, the factor of age or degree of abrasion is taken into account, the tooth library surfaces of a specific tooth type being available in all ages or degrees of abrasion, and the obtained combinations of linear factors and principal components that describe this factor are used in order to optimally adjust the abrasion for the respective remaining dentition condition.

An example embodiment depicts a new way of creating tooth restorations, in which a suggestion for the possible localizations of all contact points with the opposing tooth/teeth (ie, the contact points with the opposing jaw) is determined automatically. For this purpose, a functional bite registration and a static or occlusal bite registration are scanned, and the data sets are referenced in the same coordinate system, so that this system corresponds to the situation in the patient or in the model, and subsequently all areas or points that are at a very short distance from one registration to the other are filtered out. The decisive factor is that no contact points can or should be found outside these areas. Therefore, even the configuration of the contact points can be automated or at least substantially simplified.

An example embodiment describes a method in which the data sets of the average tooth, the generic tooth data set, the reconstructed dental prosthetic items, the tooth restorations, or the tooth models are prepared for the production process by smoothing (filtering) or by special adjustment of the tool or processing geometries. This also includes corrections of the milling machine radius, etc.

All the indicated methods are equally appropriate for inlays, onlays, partial crowns, crowns, and bridges. A further advantage, as indicated in an example embodiment, lies in the fact that, on the basis of the reconstructed occlusal surface, it is also possible to achieve a reduced occlusal surface configuration for tooth frameworks, which ensures that the tooth veneer subsequently has an approximately constant layer thickness. This can be achieved by computing the new surface at a constant distance from the reconstructed surface, or by shifting the occlusal surface toward the prepared tooth in accordance with the desired layer thickness, at least by flattening out the area of the cusps and fissures.

An example embodiment describes the use of a numerically controlled machine, by means of which, controlled by the data sets found, tooth models, tooth restorations, and dental prosthetic items are physically produced. In principle, all possible automated production methods can be used, such as CNC milling or grinding, laser treatment, stereo lithography, or lithographic sintering methods. The range of materials for the tooth restoration, dental prosthetic items, or tooth models can extend from plastics materials to metals (titanium, gold, steel, etc) to ceramics. In dentistry, a range of special materials is available for the CAD/CAM process.

Example embodiments describe devices that make it possible, for the generic tooth model data set, to directly and interactively modify the linear factors of at least the most important principal components using a control device. At the same time, the effect of this change can be observed and analyzed in a graphic display. In FIG. 18, one form of the configuration can be seen. The aforementioned devices can be used, eg, in place of automatic reconstruction and optimization, to provide dentists or dental technicians with the possibility of adjusting the generic tooth model data set to the remaining tooth situation interactively and in accordance with their own concepts.

Example embodiments describe possible methods that can be used to carry out the complete reconstruction of the occlusal surface without in the process explicitly cutting out remaining tooth structure or having to specifically mark it. Rather, the complete data set of the defective tooth is consulted (FIG. 12). By clicking on a few starting values (correspondence points) on the remaining tooth structure, a suggestion is offered, on the basis of which, for the further iteration or adaptation process, only those correspondence points are considered that are located within a specific distance between the proposed tooth surface and the defective tooth (FIG. 12). The threshold of the distance can also be varied or adjusted. In the reconstruction process, therefore, with a high degree of probability, points located in the cavity or on the ground areas of the tooth surface are not taken into account, or they are not regarded as being significant due to the fact that they are present in small numbers. The advantage of this approach lies in the fact that, as indicated in example embodiments, it is possible complete up the preparation line automatically. After the occlusal surface has been successfully reconstructed and adjusted, a search is carried out for the areas in which a transition occurs from smaller distance values (areas where remaining tooth structure is still to be found; here, generally, the reconstructed occlusal surface shows slight deviations) to areas having larger distances (areas where the tooth has been ground or tooth structure has been removed). The preparation limit or at least parts thereof must lie within these transition regions (FIG. 13). This approach can be improved if, in these regions, the locations are sought having the greatest curvature on the surface of the data set of the defective tooth, and these locations that have the greatest curvature are joined in these regions to form a line (eg, FIGS. 14 and 15). In this way, it is possible to conceive a fully automatic process, from reconstruction to identification of the preparation limit. However, it is also possible to advantageously use this as support and for formulating suggestions for further interactive processing by the user.

Example embodiments suggest an interactive possibility of inputting the preparation limit. In this context, at specific distances, points are clicked on the surface of the electronic image of the defective tooth. This clicking can take place using various control and monitoring elements, eg, computer mouse, keyboard, joystick, or 3-D mouse. A connecting line in space is interpolated between the selected points. In order to obtain points from the scanned tooth surface, the connecting line is projected onto the surface (FIG. 14). In this context, it is decisive that the direction of the projection can be selected for specific sectional areas, or even for each section.

Example embodiments describe methods that make it possible to locate and to fill in any defective areas that arise in the data set of the tooth restoration or dental prosthetic items. Such defective areas can arise, for example, if the reconstructed occlusal surface, or the reconstructed data set, does not cover the entire milled surface, or the adjustment in the region of the preparation limit was not effected in an error-free fashion, and therefore the data set in this region spreads or has errors (FIGS. 6, 8, 15). Through an automatic comparison of the preparation line with the marginal curve of the reconstructed data set, it is possible, by checking distances, to decide which regions of the lines or curves are situated too far from each other and therefore require filling or buildup (FIG. 15). Since the starting points for the preparation line and marginal curve do not have to be identical, the sections of the marginal curve of interest have to be automatically assigned to the corresponding sections of the preparation limit. For computing the built up surface, it may also be necessary, within the transitional region from one curve segment to another curve segment, to add further points on the respective curves that previously, when checking the distance, could not be assigned to the area being built up and that now make it possible to produce the most continuous possible line for computing the filled-in surface. An example embodiment explicitly describes a method of closing these defective areas (see also FIG. 16).

The results can be monitored, and further necessary interactions that should be available to the dentist or dental technician can be made possible for the operator by visualizing using 3-D glasses or 3-D monitors, etc. This is more familiar to the inexperienced operator.

When selecting the best occlusal surface, it is likewise possible to include the adjacent teeth, or antagonists, or the symmetrically opposite tooth types, by means of the generic occlusal surfaces and the associated principal components.

The present invention is presented in the description and in the Figures only by way of example on the basis of the exemplary embodiments and is not limited thereto, but rather it includes all variations, modifications, substitutions, and combinations that a person skilled in the art can derive from the present document, especially within the scope of the claims and the general representations as well as in the description of the exemplary embodiments and representations thereof in the Figures, and that those skilled in the art can combine with their expertise and knowledge of the prior art, especially taking into account the complete disclosures of previous applications that are referred to in this description. In particular, all individual features and configuration possibilities can be combined.

IN THE DRAWINGS

Further explanations will now be presented regarding the present invention and regarding the specific embodiments of the invention.

Figure 1:
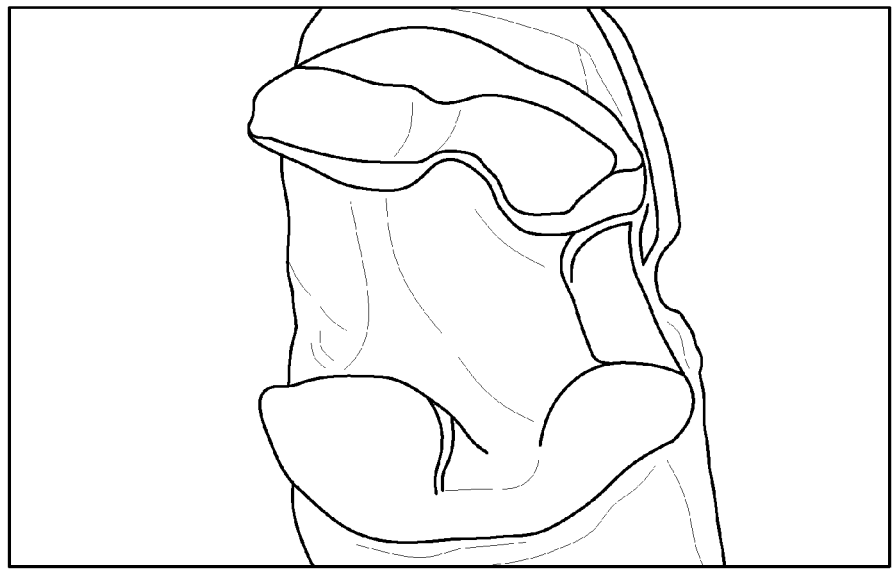
FIG. 1 depicts a defective tooth.

FIG. 1 depicts a three-dimensionally scanned defective tooth as a relief data set.

Figure 2:
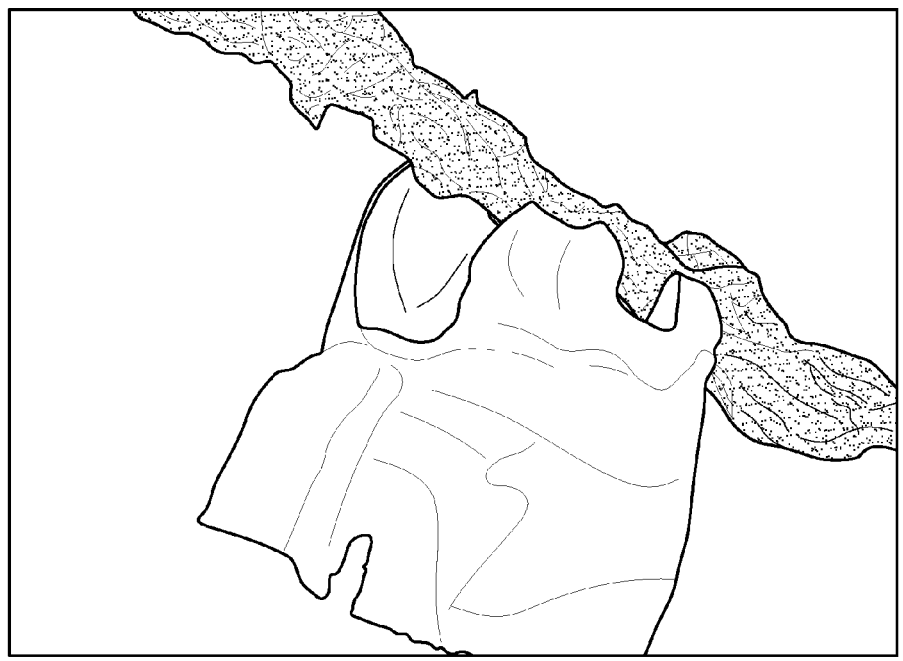
FIG. 2 depicts a bite registration that is referenced to the defective tooth.

FIG. 2 depicts a bite registration referenced to a defective tooth. This bite registration contains information regarding the antagonist. The registration involved is either of a static bite registration and/or a functional bite registration and/or the opposing tooth row. It is only important that this information be referenced in the same coordinate system as that of the tooth.

Figure 3:
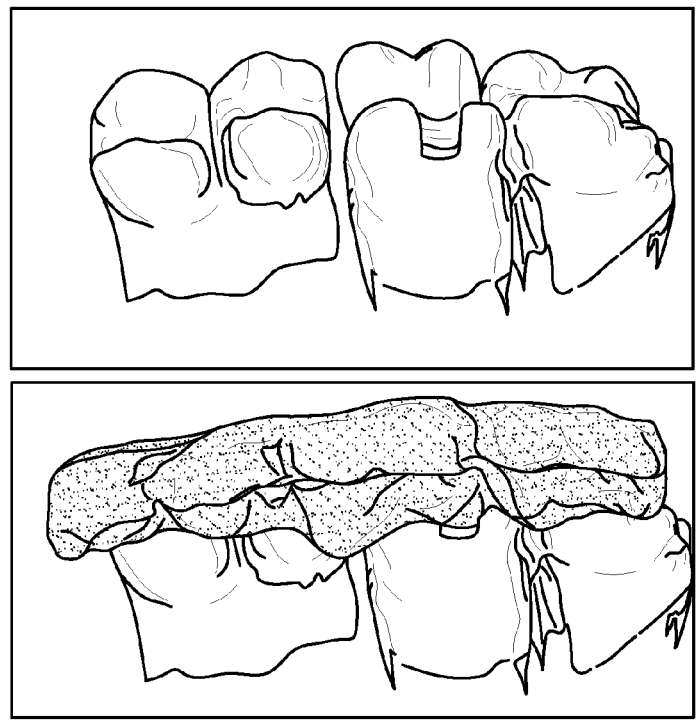
FIG. 3 depicts the tooth according to FIG. 1 represented with adjacent teeth (top) and also with the referenced bite registration (bottom)

FIG. 3 depicts the same situation as in FIG. 2, but together with the adjacent teeth (top) and an additional bite registration (bottom). The entire arrangement represents the remaining dentition condition. The adjacent teeth, for example, provide information for the mesial-distal extension of the reconstructed external shell. In addition, on the basis of the shape of the adjacent teeth, which are significant for the reconstruction in the corresponding situation, it is possible to arrive at a selection for the tooth surface (shell).

Figure 4:
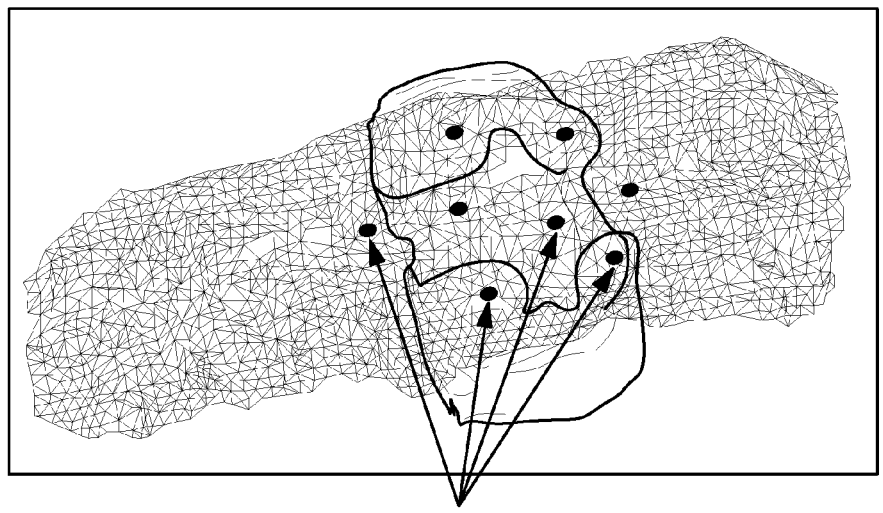
FIG. 4 is a representation of the tooth according to FIG. 1 showing a bite registration and selected correspondence points.

In FIG. 4, by marking points on the remaining tooth surface and/or contact points on the bite registration (opposing tooth row) and/or for approximal contact with the adjacent tooth, the tooth surfaces can be optimally adjusted either using a library tooth or using the generic tooth with its principal components, through an appropriate minimization of an error function. Instead of the spot markings, it is possible to select larger areas, such as remaining tooth structure and/or contact surfaces, on the basis of which the two surfaces can be adjusted by matching or by optical flow. In a further embodiment of the present invention, localizations of possible contact points can automatically be determined by comparing the functional bite registration and the static (occlusal) bite registration.

Figure 5:
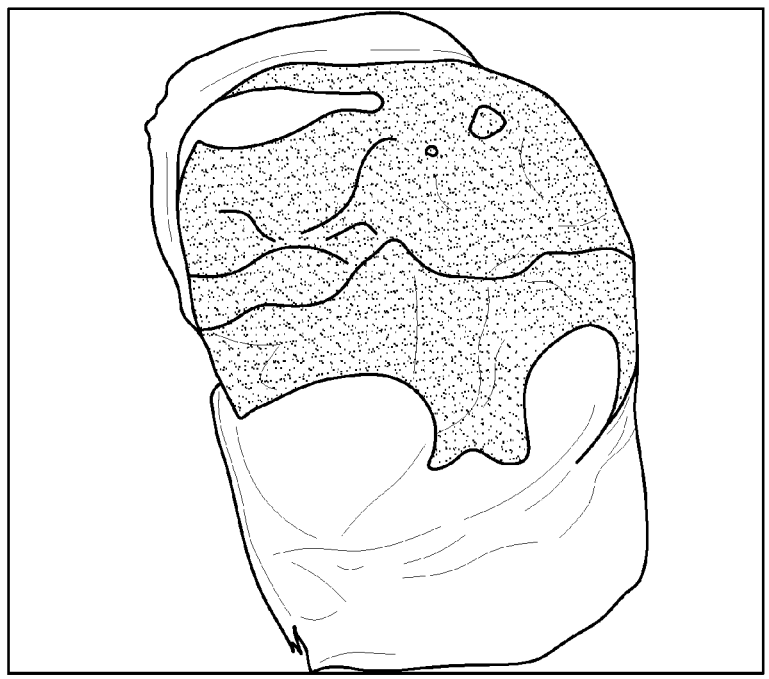
FIG. 5 depicts a tooth surface selected from a tooth library on the basis of the correspondence points.

FIG. 5 depicts an occlusal surface selected from the library and transformed to the position, or a generic occlusal surface that is adapted to the situation by optimizing the linear factors of the principal components. In both cases, a relatively good result is obtained which must be adapted to the margins and to the opposing teeth by deformation.

Figure 6:
FIG. 6 is a rotated representation of the item illustrated in FIG. 5 having recognizable defective areas.

According to FIG. 6, an adjustment of occlusal surfaces in accordance with still existing remaining tooth structure supplies missing gaps in the area that lies mainly below the tooth equator. These gaps have yet to be closed. Although the selection of complete tooth surfaces (ie, including outer areas) would be possible, it is currently expedient to separately adjust the occlusal surface and the exterior surface (oral, vestibular, and approximal surfaces). In this manner, parameters in the edge area are treated separately from parameters in the occlusal surface area, and therefore better adjustment is achieved in the individual areas. In addition, the process of completing the occlusal surfaces can be carried out automatically as mentioned in the present invention.

Figure 7:
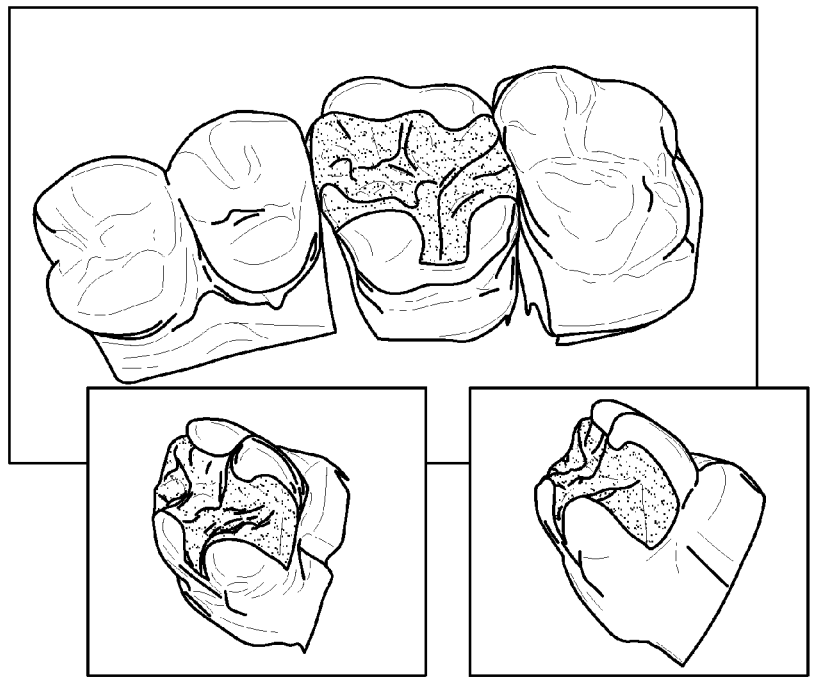
FIG. 7 depicts a fitted and completed tooth restoration.

According to FIG. 7, after adjustment to the edge/opposing tooth and after buildup of the missing surfaces, the entire exterior contour (shell) of the tooth is obtained. The important factor here is the attainment of a smooth transition in the marginal regions. By combining this data set on the preparation limit with the data set of the scanned cavity/defect, the desired model is prepared for CNC processing and production in a machine.

Figure 8:
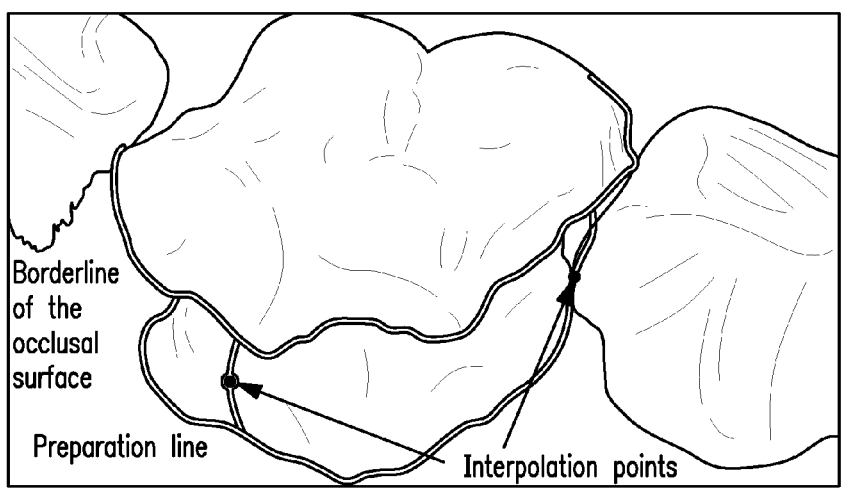
FIG. 8 depicts a fitted tooth surface for a crown preparation with an indication of the interpolation points for the reconstruction of the exterior surfaces that are still missing.

FIG. 8. If no or little remaining tooth structure is available, or only a small amount (eg, as in crown preparations), the missing exterior surfaces are built up over the entire circular area. In this context, it is expedient to indicate a few construction points. The build-up will usually run automatically. The other requirement is a smooth transition in the marginal regions.

Figure 9:
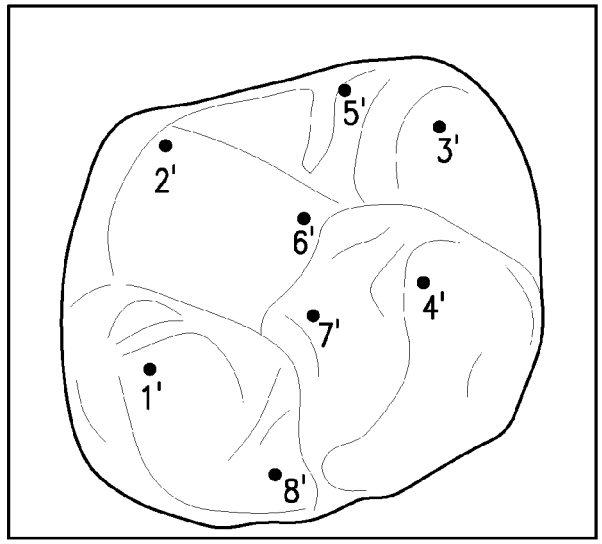
FIG. 9 is an example of a generically generated tooth surface showing correspondence points.

FIG. 9 depicts an example of a generically produced tooth surface. In this case, it is, say, an average tooth computed from 200 children's intact first upper jaw molars No. 6.

Figure 10:
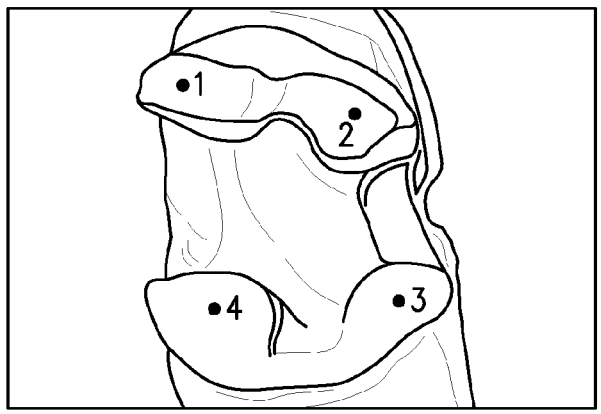
FIG. 10 depicts a defective tooth having the correspondence points indicated in FIG. 9.
Figure 11:
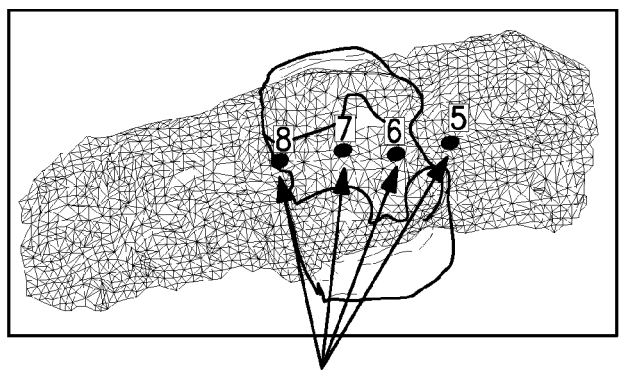
FIG. 11 depicts a defective tooth with bite registration and having the correspondence points according to FIG. 9.
Figure 12:
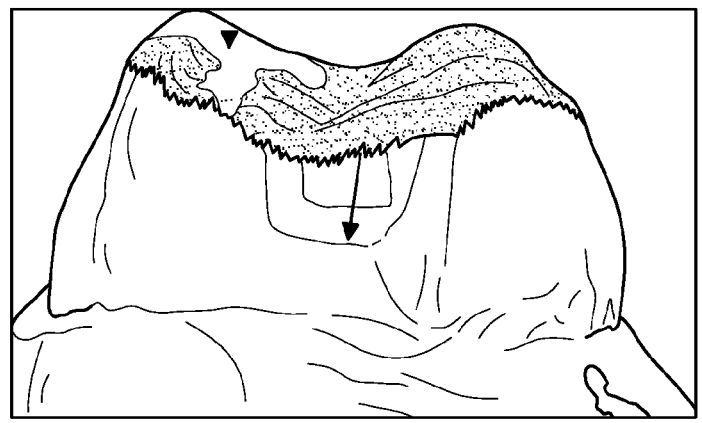
FIG. 12 depicts an example for distinguishing the areas covering the milled tooth structure and requiring filling by a tooth restoration, and covering the intact remaining tooth structure, on the basis of distance checking during the process of reconstructing and adjusting the shell.
Figure 13:
FIG. 13 depicts an example for detecting the preparation limit in the transition region between the two previously distinguished areas.
Figure 14:
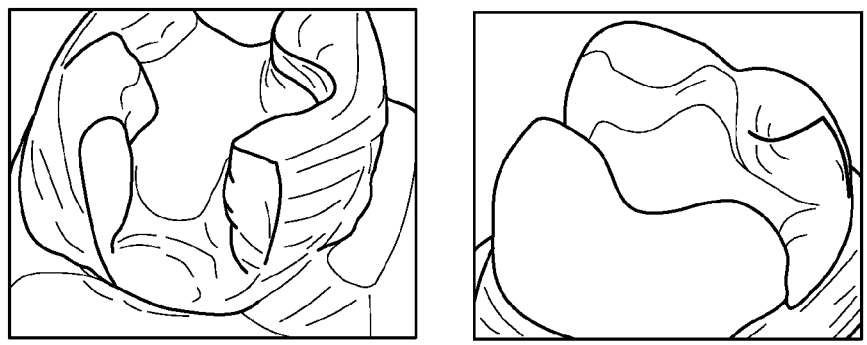
FIG. 14 depicts an example of interactive marking of the preparation limit in varying views and of projecting the connecting line onto the tooth surface.
Figure 15:
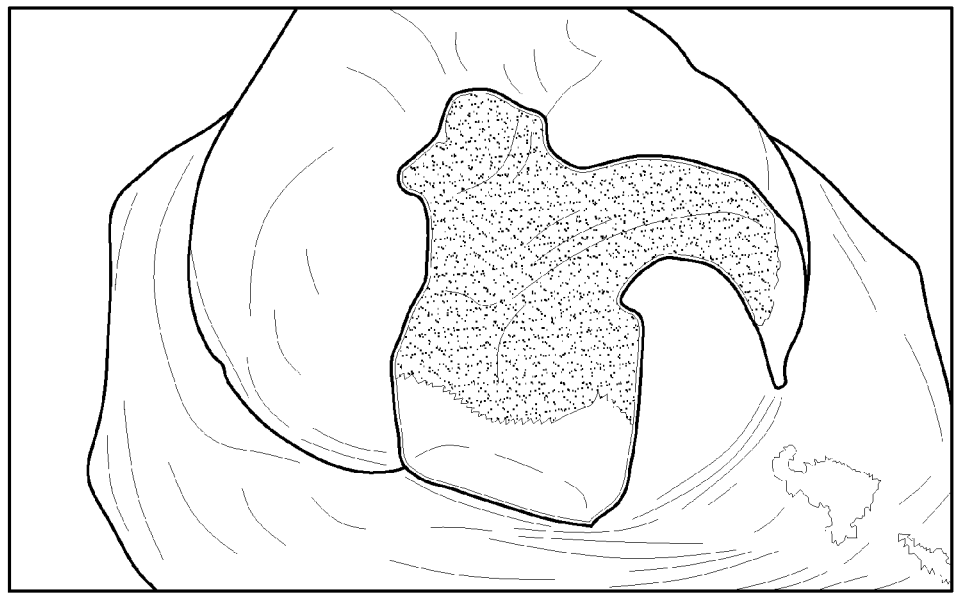
FIG. 15 depicts an example of locating areas still requiring build-up by comparison of the two marginal curves.
Figure 16:
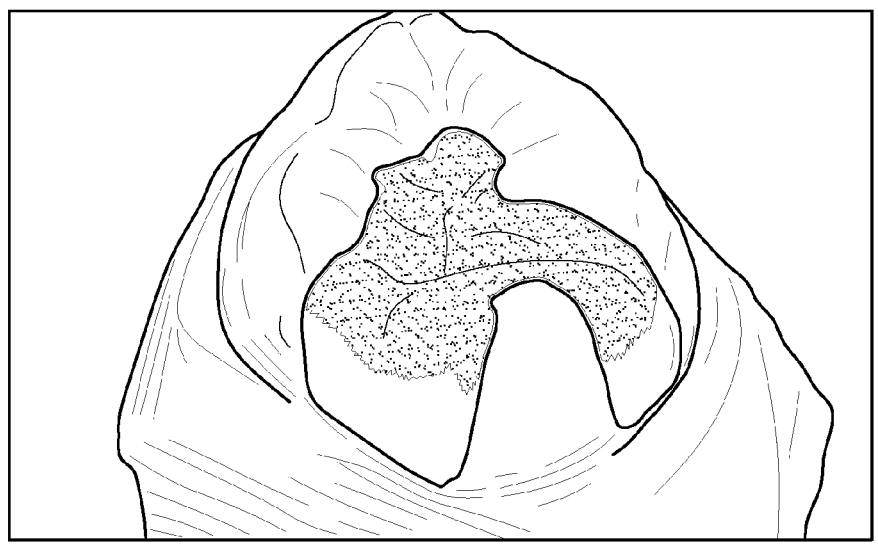
FIG. 16 depicts a complete tooth restoration in which the areas still missing have been automatically built up.
Figure 17:
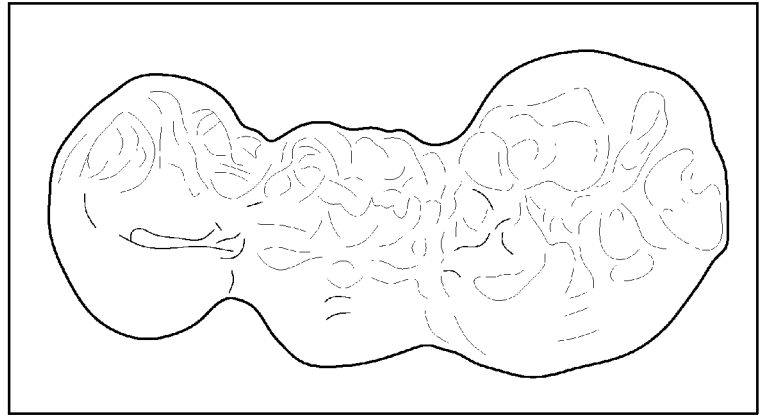
FIG. 17 depicts an example of a tooth restoration that has been carried out in a machine in accordance with the generic tooth model method.
Figure 18:
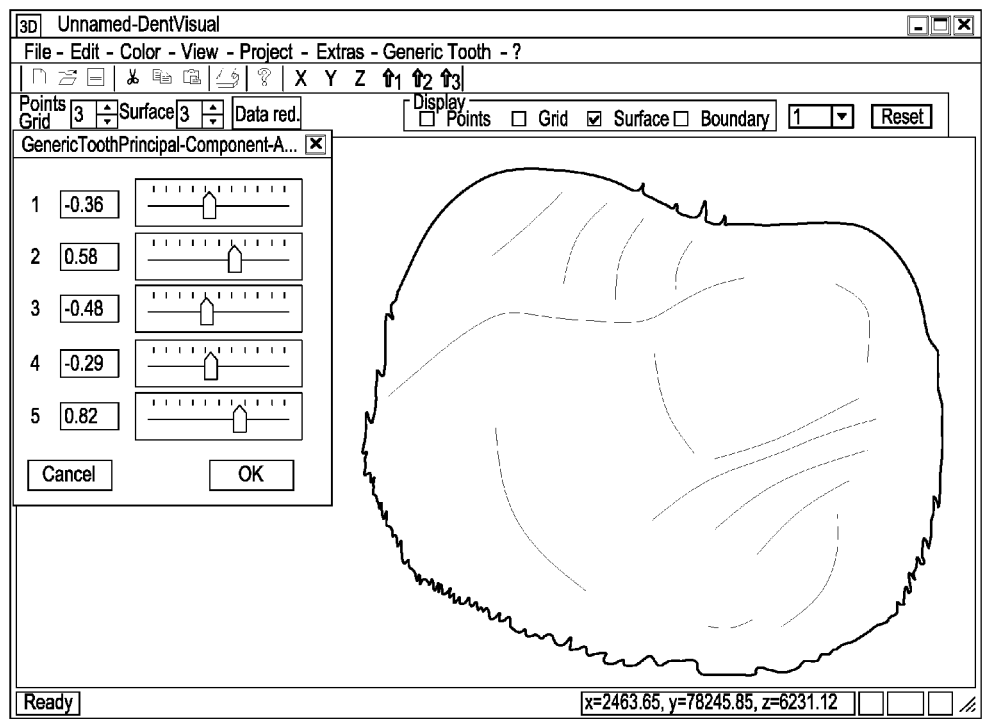
FIG. 18 depicts an example for a control device for modifying the linear factors and simultaneously illustrating the modification.
Figure 19:
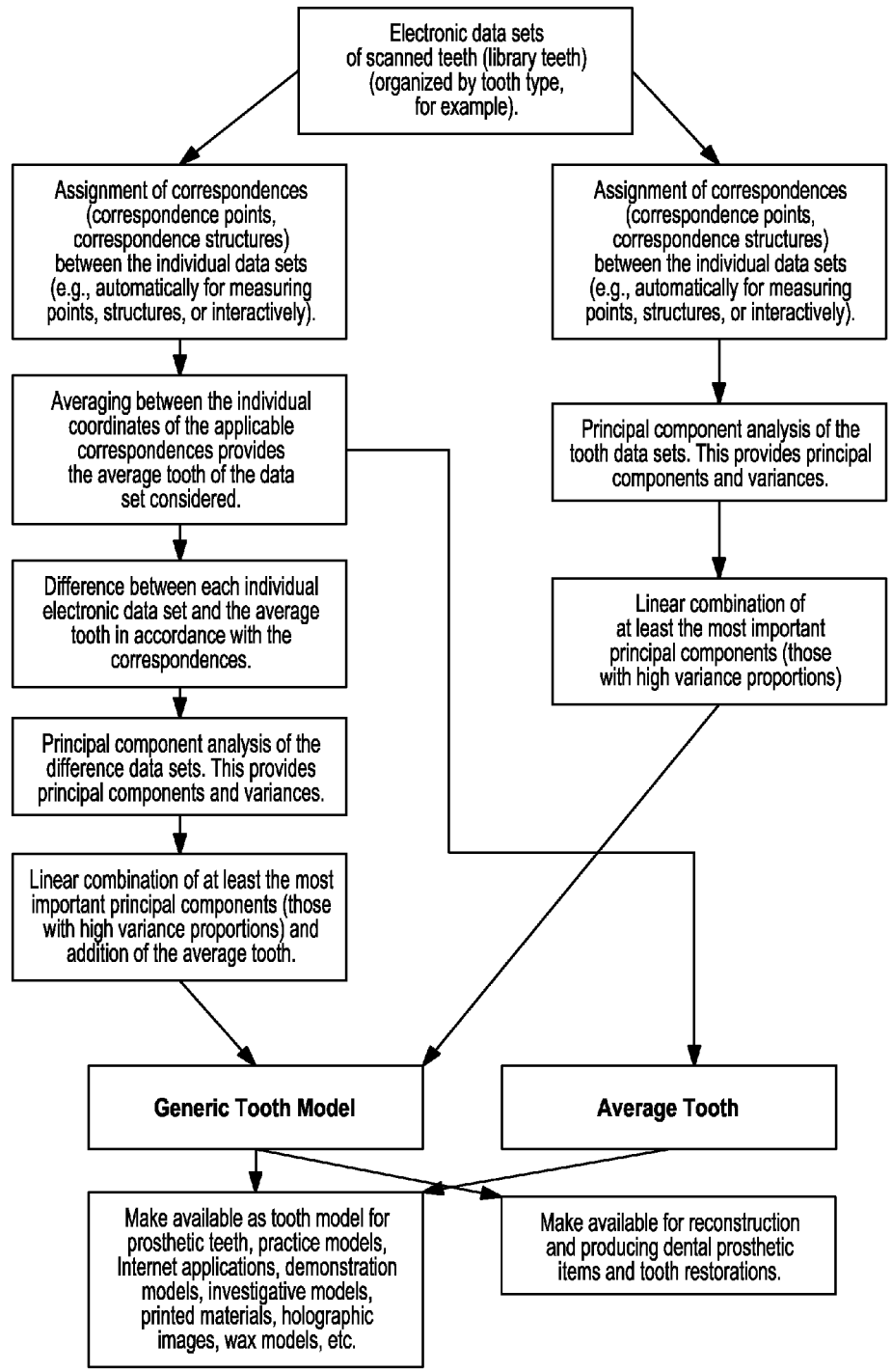
FIG. 19 is a flow chart for the creation of an average data set or a generic tooth model data set.
Figure 20:
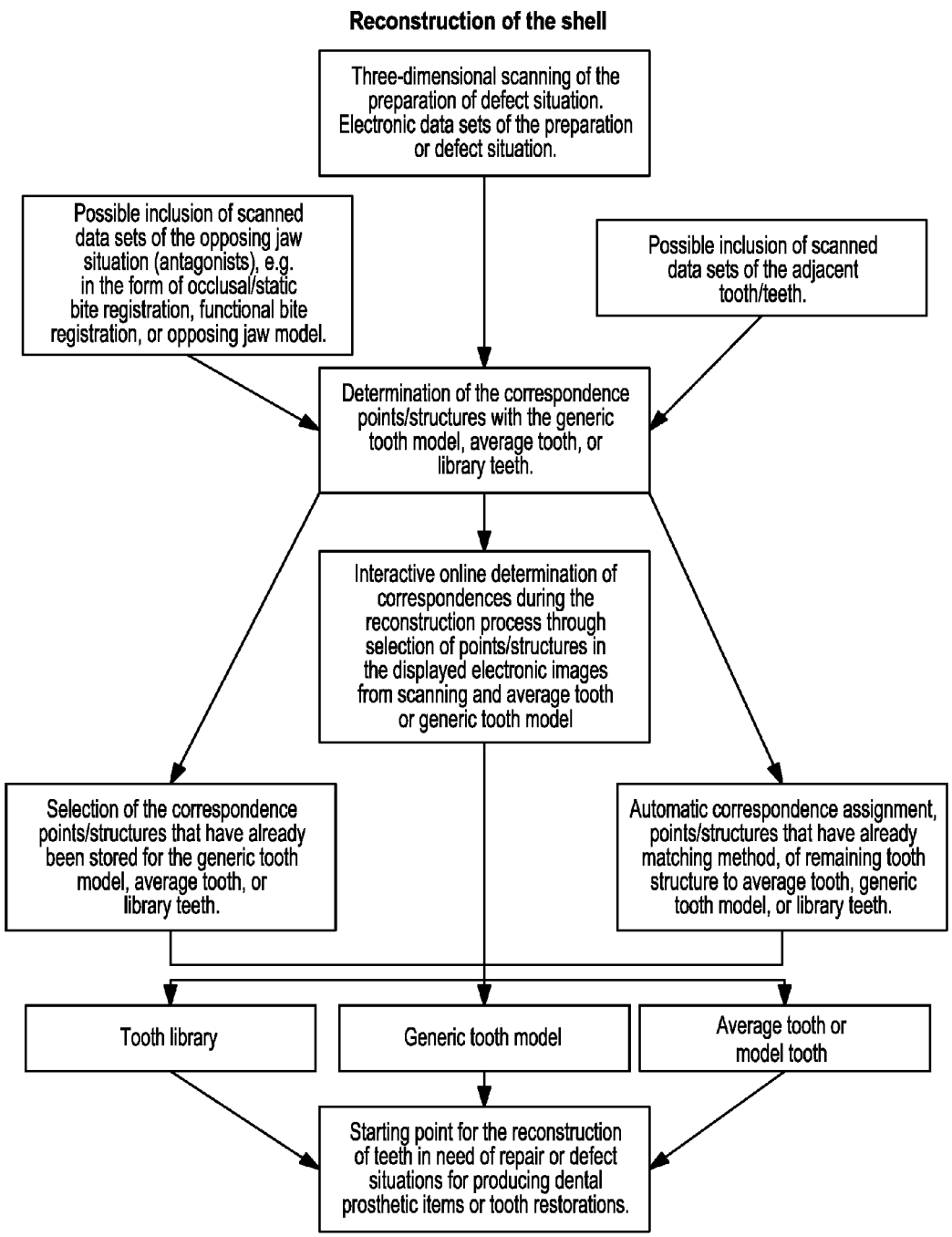
FIG. 20 depicts a flow chart for the reconstruction of a shell.
Figure 21:
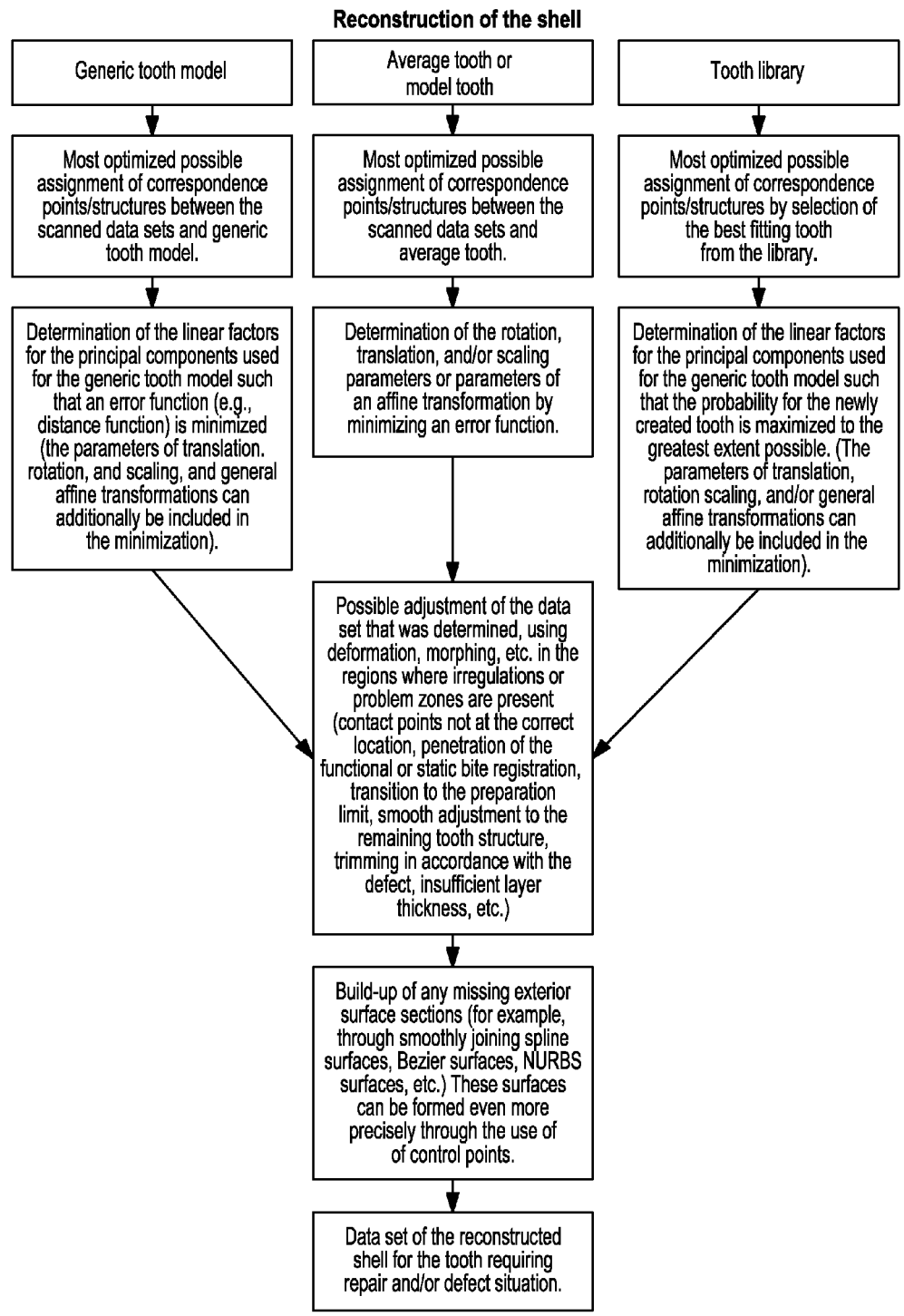
FIG. 21 depicts a continuation of the flow chart of FIG. 14 for the reconstruction of a shell.
Figure 22:
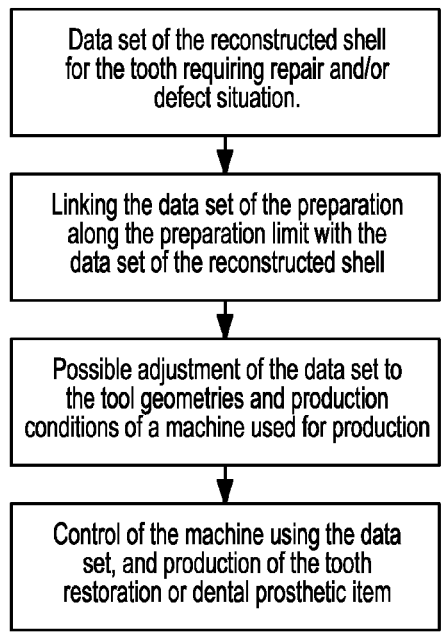
FIG. 22 depicts a flow chart for the production of a dental prosthetic item or a tooth restoration.
Figure 23:
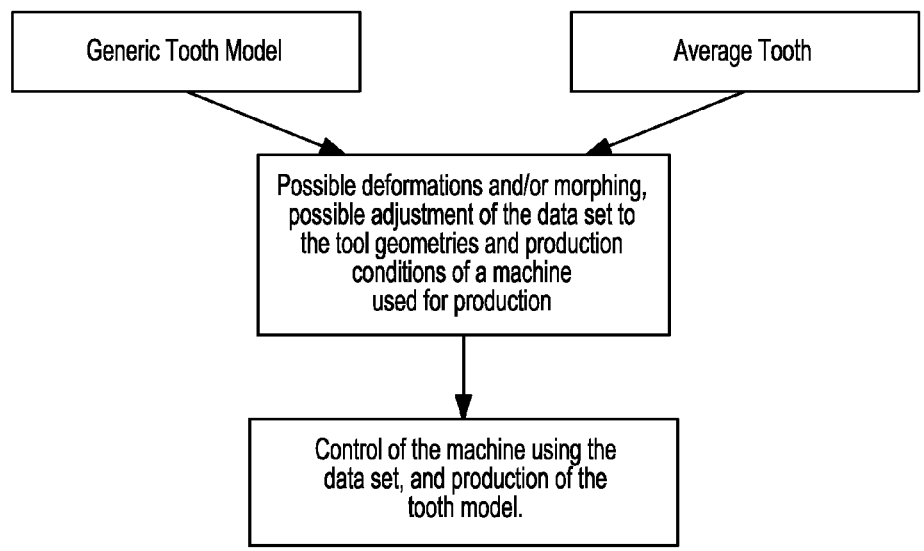
FIG. 23 is a flow chart for the production of a tooth model.

FIGS. 10 and 11: The generic occlusal surface with its principal components can in turn be adjusted to the remaining dentition condition by implementing the remaining tooth structure (FIG. 10) and/or by selecting specific points on the bite registration (FIG. 11) and/or adjacent teeth, etc. In contrast to the direct use of a tooth library, it is possible, using the generic tooth model data set, to select contact points or contact structures or feature points or feature structures immediately before the computation and design processes, since it is sufficient to mark these points on the generic tooth. In the tooth library, on the other hand, it would be necessary to provide each individual tooth with the new feature points.

Therefore, this permits a rapid change in accordance with the situation in order to realize various occlusion and shape concepts.

The invention claimed is:

1. A method of creating an electronic data set of a natural looking tooth model for creating a dental prosthetic item, a tooth restoration, or a tooth model, said method comprising steps of:
   a) scanning a predetermined minimum number of teeth of a same tooth type to provide a multiplicity of electronic data sets of the tooth type;
   b) for each individual electronic data set, assigning at least a certain number of at least one of correspondence points and correspondence structures that are characterized for the tooth type in the individual electronic data sets;
   c) performing a principal component analysis for at least one of the assigned correspondence points and correspondence structures of the scanned teeth to generate principle components for the tooth type; and
   d) performing a linear combination of at least a portion of the resulting principal components for the tooth type of interest and making the linear combination available as a generic natural looking tooth model data set,
   wherein at least one of steps a), b), c), and d) is performed by a computer.

2. The method as defined in claim 1, wherein the assigning of at least one of the correspondence points and correspondence structures is performed automatically.

3. The method as defined in claim 1, wherein, for the assigning of at least one of the correspondence points and correspondence structures, a weighted combination is used taken from at least one of height values, gradients, and curvatures of corresponding electronic data.

4. The method as defined in claim 1, wherein the assigning of at least one of the correspondence points and correspondence structures is performed automatically.

5. The method as defined in claim 1, wherein, for the assigning of at least one of the correspondence points and correspondence structures, a weighted combination is used taken from at least one of height values, gradients, and curvatures of the corresponding electronic data.

6. A method of using an electronic representation of an average tooth or generic tooth model, as obtained using a method as defined in claim 1, as an electronic template for the creation of physical tooth models, tooth restorations, or dental prosthetic items using a machine that is controlled by the average data set, or generic tooth model data set, or by parts of these data sets.

7. A method of creating physical dental prosthetic items or tooth restorations for defective teeth or for defective dental prosthetic items, using an electronic representation of an average tooth, or generic tooth model, as obtained using a method as defined in claim 1, said method comprising the steps of:
   a) carrying out a three-dimensional scan of a preparation of the defective tooth or of a defective dental prosthetic item, and creating an electronic data set representing the preparation or defective dental prosthetic item;
   b) selecting at least one of characteristic correspondence points and correspondence structures from the electronic information of the scanned preparation, or of the scanned defective dental prosthetic item, for the tooth type of the defective tooth, or for the tooth type appropriate to the defective dental prosthetic item;
   c) assigning at least one of the correspondence points and the correspondence structures in the electronic data sets of the scanned preparation or defective dental prosthetic item in accordance with at least one of the correspondence points and correspondence structures in the data set of the average tooth, or the generic tooth model;

d) approximating at least one of the correspondence points and correspondence structures that are assigned to each other to the greatest extent possible using an optimization method;

e) making the data set obtained by the optimization the basis of the reconstruction of the missing part of the defective tooth, or for building up the defective dental prosthetic item; and f) creating a physical dental prosthetic item or a physical tooth restoration for the defective tooth or for the defective dental prosthetic item using a machine that is controlled in accordance with the data set obtained in step e).

8. A method for creating a three-dimensional electronic data set of a generic tooth model, said method comprising steps of:

a) generating a plurality of electronic data sets of a certain tooth type by scanning a predetermined minimum number of teeth of a same tooth type;

b) for each individual electronic data set, assigning at least a certain number of at least one of correspondence points and correspondence structures that are characterized for the tooth type in the individual electronic data set, wherein the correspondence points and correspondence structures assigned for the individual electronic data set identify correspondences between points and structures of the individual electronic data set and points and structures of other electronic data sets, c) creating an average value from the electronic data sets based on the assigning of the at least one of said correspondence points and correspondence structures in each of the individual electronic data sets; and d) making available an average electronic data set derived from said average value as an electronic representation of a natural looking tooth having an average tooth surface with respect to the scanned teeth, wherein, after the assigning of at least one of the correspondence points and correspondence structures, a plurality of difference data sets are created by subtracting the average electronic data set from each of the electronic data sets, and subsequently, a principal component analysis is performed for the difference data sets, a linear combination of at least a portion of resulting principal components is performed for the tooth type, and the linear combination is made available, together with the average data set, as a generic tooth model data set, wherein at least one of steps a), b), c), and d) is performed by a computer.

9. The method as defined in claim 8, wherein the assigning of at least one of the correspondence points and correspondence structures is performed automatically.

10. The method as defined in claim 8, wherein, for the assigning of at least one of the correspondence points and correspondence structures, a weighted combination is used taken from at least one of height values, gradients, and curvatures of corresponding electronic data.

11. A method of creating an electronic data set of a natural looking tooth model for creating a dental prosthetic item, a tooth restoration, or a tooth model, said method comprising steps of:

a) specifying a combination of different tooth types;

b) scanning a predetermined minimum number of teeth of a same combination of different tooth types to provide a multiplicity of electronic data sets of the specified combination;

c) for each individual electronic data set, assigning at least a certain number of at least one of correspondence points and correspondence structures that are characterized for the combination of different tooth types in the individual electronic data sets;

d) performing a principal component analysis for at least one of the assigned correspondence points and correspondence structures of the scanned teeth to generate principle components for the combination of different tooth types; and e) performing a linear combination of at least a portion of the resulting principal components for the combination of different tooth types and making the linear combination available as a generic natural looking tooth model data set with a correlated combination of different tooth types, wherein at least one of steps a), b), c), d), and e) is performed by a computer.

* * * * *